United States Patent [19]

Dreikorn

[11] 4,084,004

[45] Apr. 11, 1978

[54] RODENTICIDAL USE OF DIPHENYLAMINES

[75] Inventor: Barry Allen Dreikorn, Indianapolis, Ind.

[73] Assignee: Eli Lilly and Company, Indianapolis, Ind.

[21] Appl. No.: 706,021

[22] Filed: Jul. 21, 1976

Related U.S. Application Data

[63] Continuation-in-part of Ser. No. 617,115, Sep. 26, 1975, abandoned.

[51] Int. Cl.$^2$ .......................... A01N 17/14; A01N 9/20
[52] U.S. Cl. ..................................... 424/330; 424/84; 424/304
[58] Field of Search .......................... 424/84, 304, 330

[56] References Cited

U.S. PATENT DOCUMENTS

| 3,948,990 | 4/1976 | Barlow et al. | 424/330 |
| 3,950,377 | 4/1976 | Barlow | 424/304 |

OTHER PUBLICATIONS

Van Esch et al., "Nature", (1957), vol. 180, pp. 509–510.

*Primary Examiner*—V. D. Turner
*Attorney, Agent, or Firm*—Joseph A. Jones; William E. Maycock

[57] ABSTRACT

A group of diphenylamines, having trinitro substitution or dinitro-trifluoromethyl substitution on one ring and from 1 to 5 substituents of a defined class, particularly halogen atoms, on the other ring, are useful rodenticides.

37 Claims, No Drawings

RODENTICIDAL USE OF DIPHENYLAMINES

CROSS REFERENCE

This application is a continuation-in-part of my copending application Ser. No. 617,115, filed Sept. 26, 1975, now abandoned.

BACKGROUND OF THE INVENTION

This invention belongs to the rodenticidal art and provides a new method and compositions for reducing populations or rats or mice.

It has long been known that rats and mice must be controlled. Rats and mice are known carriers of many diseases of which bubonic plague is only the best known. The pestiferous animals also, when sharing the habitations of mankind, soil and contaminate the areas in which they live, and destroy buildings and their contents by their tunneling and nest-building. The animals also consume foodstuffs, and contaminate what they do not consume. A colony of rats in a grain-storage building can consume or destroy substantial amounts of food.

Many kinds of rodenticides have been, and still are, in use. Metallic poisons, such as arsenic and thallium compounds, are still in use, but obviously pose serious hazards to people and useful animals. Organic chemical poisons, of which warfarin is the best known, are in extremely wide use and have served well. However, rodents are developing resistance to such poisons.

Rodenticides are usually presented to rats or mice in the form of mixtures with foodstuffs. The concentration of rodenticide in the mixture is adjusted so that the rodents consume an amount of the rodenticide which is either acutely or chronically lethal. It is advisable not to make the mixture so concentrated that the rodent dies immediately, or even soon after eating. Rodents, and especially rats, are intelligent enough to understand the casual relationship between feeding and death if the time interval is very short. Thus, the best practice is to adjust the concentration of the rodenticide so that the rodents will be poisoned over a number of feedings at the poison bait.

In special circumstances, rodenticides are sometimes mixed in drinking water, or prepared as "tracking powders", which are deposited in runways used by the rodents. After the animals have walked through the loose poison powder, they lick their feet clean and thus ingest the rodenticide.

Compounds such as those used in the present invention have not previously been used for the control of rodents. The compounds are known to be fungicides and insecticides, however. Therefore, prior workers have made formulations which comprised the compounds dispersed in water and in finely powdered solids. South African Patents Nos. 73/09415 and 72/01370 supply the history of the compounds.

SUMMARY OF THE INVENTION

The present invention is a method of reducing a population of rats or mice which comprises supplying to a locus frequented by the rats or mice a rodenticidal composition which comprises a foodstuff and an effective rodenticidal concentration of a compound of the formula

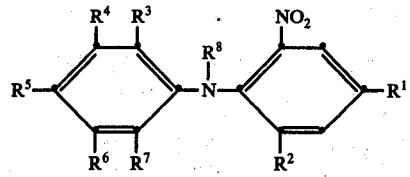

wherein one of $R^1$ and $R^2$ represents nitro and the other represents trifluoromethyl or nitro; $R^8$ represents hydrogen, methyl, ethyl or propyl, provided that $R^8$ represents hydrogen when either $R^1$ or $R^2$ represents trifluoromethyl;

(1) when $R^1$ represents trifluoromethyl, $R^3$, $R^4$, $R^5$, $R^6$ and $R^7$ all represent chloro, all represent bromo, or all represent fluoro, or $R^4$ and $R^6$ represent trifluoromethyl and $R^3$, $R^5$ and $R^7$ represent hydrogen;

(2) when $R^2$ represents trifluoromethyl, $R^5$ represents halo, hydrogen, cyano, nitro, methyl or trifluoromethyl; $R^3$ and $R^7$ independently represent chloro, bromo, fluoro, methyl, trifluoromethyl, nitro or hydrogen; $R^4$ and $R^6$ independently represent chloro, bromo, fluoro, methyl, trifluoromethyl or hydrogen; provided that (a) when $R^3$, $R^4$, $R^6$ and $R^7$ all represent hydrogen, $R^5$ does not represent fluoro, methyl or hydrogen;

(b) when $R^5$ represents hydrogen, no more than two or $R^3$, $R^4$, $R^6$ and $R^7$ represent hydrogen;

(c) no more than two of $R^3$, $R^4$, $R^5$, $R^6$ and $R^7$ represent trifluoromethyl;

(d) when one and only one of $R^3$, $R^4$, $R^6$ and $R^7$ represents trifluoromethyl, two or three of $R^3$, $R^5$ and $R^7$ represent chloro or bromo;

(e) no more than one of $R^3$, $R^4$, $R^5$, $R^6$ and $R^7$ represents methyl, except that $R^4$ and $R^6$ both may represent methyl;

(f) when $R^3$, $R^4$, $R^5$, $R^6$ or $R^7$ represents methyl, two or three of $R^3$, $R^5$ and $R^7$ represent chloro, bromo or fluoro;

(g) no more than one of $R^3$ and $R^7$ represents nitro;

(h) when $R^3$ or $R^7$ represents nitro, $R^5$ represents chloro, bromo or nitro;

(3) when both $R^1$ and $R^2$ represent nitro and $R^8$ represents hydrogen, $R^5$ represents halo, hydrogen, cyano, nitro or trifluoromethyl; $R^3$ and $R^7$ independently represent bromo, chloro, fluoro, hydrogen or nitro; $R^4$ and $R^6$ independently represent chloro, bromo, fluoro, trifluoromethyl or hydrogen; provided that (a) no more than two of $R^3$, $R^4$, $R^5$, $R^6$ and $R^7$ represent hydrogen, except that $R^3$, $R^5$ and $R^7$ all represent hydrogen when $R^4$ and $R^6$ both represent trifluoromethyl;

(b) no more than one of $R^3$, $R^5$ and $R^7$ represents nitro;

(c) when two of $R^3$, $R^4$, $R^5$, $R^6$ and $R^7$ represent hydrogen, they are not adjacent to each other;

(d) when either $R^3$ or $R^7$ represents nitro, neither $R^5$ nor the other of $R^3$ and $R^7$ represents hydrogen;

(e) $R^5$ does not represent cyano, nitro or trifluoromethyl when $R^4$ or $R^6$ represents trifluoromethyl;

(4) when $R^8$ does not represent hydrogen, $R^3$, $R^4$, $R^5$, $R^6$ and $R^7$ independently represent chloro, bromo, fluoro or hydrogen, provided that no more than two of $R^3$, $R^4$, $R^5$, $R^6$ and $R^7$ represent hydrogen, and two such hydrogen atoms are not adjacent to each other; provided that, in classes (3) and (4) above, (a) when $R^3$, $R^4$, $R^5$, $R^6$ or $R^7$ represents fluoro, two or three of $R^3$, $R^5$ and $R^7$ represent chloro or bromo;

and provided that, in clases 2), 3) and 4) above, (a) when $R^3$, $R^4$, $R^5$, $R^6$ or $R^7$ represents trifluoromethyl, none of $R^3$, $R^4$, $R^5$, $R^6$ and $R^7$ represents fluoro or methyl.

The invention also provides rodenticidal compositions which comprise an inert carrier and a rodenticidally-effective concentration of a compound described above.

DESCRIPTION OF THE PREFERRED EMBODIMENT

All of the compounds below will be named as diphenylamines for the sake of consistency and clarity, even though some compounds may be named otherwise according to the rules of nomenclature.

All percentages and parts described hereafter refer to percentages and parts by weight.

The term halo refers to chloro, bromo, fluoro and iodo.

It will be understood that the present invention may be practiced in a number of different ways, making use of different types or classes of compounds. For example, the following classes of compounds of the invention are contemplated for use in the method and as components of the rodenticidal compositions of the invention. Each numbered subparagraph below describes an independent class of compounds of the invention; in each class, the variable substituents have the general meanings above if not otherwise stated. Compounds wherein:

1. $R^1$ represents trifluoromethyl;
2. $R^2$ represents trifluoromethyl;
3. $R^1$ and $R^2$ both represent nitro;
4. $R^8$ represents hydrogen;
5. $R^8$ represents methyl, ethyl or propyl;
6. $R^8$ represents methyl;
7. $R^8$ represents ethyl or propyl;

Compounds of subparagraphs 2 and 4 wherein:

8. $R^5$ represents halo, hydrogen, cyano, nitro, methyl or trifluoromethyl;
9. $R^5$ represents halo, hydrogen, cyano, nitro or trifluoromethyl;
10. $R^5$ represents halo, hydrogen, cyano, nitro or methyl;
11. $R^5$ represents halo, hydrogen, cyano, methyl or trifluoromethyl;
12. $R^5$ represents halo, hydrogen, nitro, methyl or trifluoromethyl;
13. $R^5$ represents halo, cyano, nitro, or trifluoromethyl;
14. $R^5$ represents halo, hydrogen or nitro;
15. $R^5$ represents halo, hydrogen or trifluoromethyl;
16. $R^5$ represents halo or hydrogen;
17. $R^5$ represents chloro, bromo or fluoro;
18. $R^5$ represents chloro or bromo;
19. $R^3$, $R^4$, $R^6$ and $R^7$ independently represent chloro, bromo, fluoro, methyl, trifluoromethyl or hydrogen;
20. $R^3$, $R^4$, $R^6$ and $R^7$ independently represent chloro, bromo, fluoro, methyl or hydrogen;
21. $R^3$, $R^4$, $R^6$ and $R^7$ independently represent chloro, bromo, fluoro, trifluoromethyl or hydrogen;
22. $R^3$, $R^4$, $R^6$ and $R^7$ independently represent chloro, bromo, fluoro or hydrogen;
23. $R^3$, $R^4$, $R^6$ and $R^7$ independently represent chloro, bromo or hydrogen;
24. $R^3$, $R^4$, $R^6$ and $R^7$ independently represent methyl, trifluoromethyl or hydrogen;
25. $R^3$, $R^4$, $R^6$ and $R^7$ independently represent methyl or hydrogen;
26. $R^3$, $R^4$, $R^6$ and $R^7$ independently represent trifluoromethyl or hydrogen;
27. $R^3$, $R^5$ and $R^7$ independently represent chloro, bromo, fluoro, trifluoromethyl, nitro or hydrogen;
28. $R^3$, $R^5$ and $R^7$ independently represent chloro, bromo, fluoro, nitro or hydrogen;
29. $R^3$, $R^5$ and $R^7$ independently represent chloro, bromo, fluoro, nitro or trifluoromethyl;
30. $R^3$, $R^5$ and $R^7$ independently represent chloro, bromo or fluoro;
31. $R^3$, $R^5$ and $R^7$ independently represent chloro, bromo or trifluoromethyl;
32. $R^3$, $R^5$ and $R^7$ independently represent chloro or bromo;
33. $R^4$ and $R^6$ independently represent chloro, bromo, fluoro, methyl or hydrogen;
34. $R^4$ and $R^6$ independently represent chloro, bromo, fluoro, trifluoromethyl or hydrogen;
35. $R^4$ and $R^6$ independently represent chloro, bromo, fluoro or hydrogen;
36. $R^4$ and $R^6$ independently represent methyl, trifluoromethyl or hydrogen;
37. $R^4$ and $R^6$ independently represent chloro or bromo;

Compounds of subparagraphs 3 and 4 wherein:

38. $R^5$ represents halo, hydrogen, cyano or nitro;
39. $R^5$ represents halo, hydrogen, nitro or trifluoromethyl;
40. $R^5$ represents halo, hydrogen, cyano or trifluoromethyl;
41. $R^5$ represents chloro, bromo, fluoro, hydrogen or nitro;
42. $R^5$ represents chloro, bromo, fluoro, hydrogen, nitro or trifluoromethyl;
43. $R^5$ represents chloro, bromo, fluoro, hydrogen or trifluoromethyl;
44. $R^3$ and $R^7$ independently represent bromo, chloro, fluoro or hydrogen;
45. $R^3$ and $R^7$ independently represent bromo, chloro, fluoro or nitro;
46. $R^3$ and $R^7$ independently represent bromo, chloro or fluoro;
47. $R^4$ and $R^6$ independently represent chloro, bromo, fluoro or trifluoromethyl;
48. $R^4$ and $R^6$ independently represent chloro, bromo, fluoro or hydrogen;
49. $R^4$ and $R^6$ independently represent chloro, bromo or fluoro; Compounds of subparagraph 3 and one of subparagraphs 5, 6 and 7 wherein:
50. $R^3$, $R^4$, $R^5$, $R^6$ and $R^7$ independently represent chloro, bromo or fluoro;
51. $R^3$, $R^4$, $R^5$, $R^6$ and $R^7$ independently represent chloro, bromo or hydrogen;
52. $R^3$, $R^4$, $R^5$, $R^6$ and $R^7$ independently represent chloro or bromo;
53. $R^3$, $R^5$ and $R^7$ independently represent chloro, bromo, fluoro or hydrogen;
54. $R^3$, $R^5$ and $R^7$ independently represent chloro, bromo or fluoro;
55. $R^3$, $R^5$ and $R^7$ independently represent chloro or bromo;
56. $R^4$ and $R^6$ independently represent chloro, bromo, fluoro or hydrogen;

57. $R^4$ and $R^6$ independently represent chloro, bromo or hydrogen;
58. $R^4$ and $R^6$ independently represent chloro or bromo;
59. $R^4$ and $R^6$ independently represent hydrogen;
60. compounds of subparagraphs 2, 4, 8 and 19;
61. compounds of subparagraphs 2, 4, 8 and 20;
62. compounds of subparagraphs 2, 4, 8 and 21;
63. compounds of subparagraphs 2, 4, 8 and 22;
64. compounds of subparagraphs 2, 4, 8 and 23;
65. compounds of subparagraphs 2, 4, 8 and 24;
66. compounds of subparagraphs 2, 4, 8 and 25;
67. compounds of subparagraphs 2, 4, 8 and 26;
68. compounds of subparagraphs 2, 4, 9 and 19;
69. compounds of subparagraphs 2, 4, 9 and 20;
70. compounds of subparagraphs 2, 4, 9 and 21;
71. compounds of subparagraphs 2, 4, 9 and 22;
72. compounds of subparagraphs 2, 4, 9 and 23;
73. compounds of subparagraphs 2, 4, 9 and 24;
74. compounds of subparagraphs 2, 4, 9 and 25;
75. compounds of subparagraphs 2, 4, 9 and 26;
76. compounds of subparagraphs 2, 4, 10 and 19;
77. compounds of subparagraphs 2, 4, 10 and 20;
78. compounds of subparagraphs 2, 4, 10 and 21;
79. compounds of subparagraphs 2, 4, 10 and 22;
80. compounds of subparagraphs 2, 4, 10 and 23;
81. compounds of subparagraphs 2, 4, 10 and 24;
82. compounds of subparagraphs 2, 4, 10 and 25;
83. compounds of subparagraphs 2, 4, 10 and 26;
84. compounds of subparagraphs 2, 4, 11 and 19;
85. compounds of subparagraphs 2, 4, 11 and 20;
86. compounds of subparagraphs 2, 4, 11 and 21;
87. compounds of subparagraphs 2, 4, 11 and 22;
88. compounds of subparagraphs 2, 4, 11 and 23;
89. compounds of subparagraphs 2, 4, 11 and 24;
90. compounds of subparagraphs 2, 4, 11 and 25;
91. compounds of subparagraphs 2, 4, 11 and 26;
92. compounds of subparagraphs 2, 4, 12 and 19;
93. compounds of subparagraphs 2, 4, 12 and 20;
94. compounds of subparagraphs 2, 4, 12 and 21;
95. compounds of subparagraphs 2, 4, 12 and 22;
96. compounds of subparagraphs 2, 4, 12 and 23;
97. compounds of subparagraphs 2, 4, 12 and 24;
98. compounds of subparagraphs 2, 4, 12 and 25;
99. compounds of subparagraphs 2, 4, 12 and 26;
100. compounds of subparagraphs 2, 4, 13 and 19;
101. compounds of subparagraphs 2, 4, 13 and 20;
102. compounds of subparagraphs 2, 4, 13 and 21;
103. compounds of subparagraphs 2, 4, 13 and 22;
104. compounds of subparagraphs 2, 4, 13 and 23;
105. compounds of subparagraphs 2, 4, 13 and 24;
106. compounds of subparagraphs 2, 4, 13 and 25;
107. compounds of subparagraphs 2, 4, 13 and 26;
108. compounds of subparagraphs 2, 4, 14 and 19;
109. compounds of subparagraphs 2, 4, 14 and 20;
110. compounds of subparagraphs 2, 4, 14 and 21;
111. compounds of subparagraphs 2, 4, 14 and 22;
112. compounds of subparagraphs 2, 4, 14 and 23;
113. compounds of subparagraphs 2, 4, 14 and 24;
114. compounds of subparagraphs 2, 4, 14 and 25;
115. compounds of subparagraphs 2, 4, 14 and 26;
116. compounds of subparagraphs 2, 4, 15 and 19;
117. compounds of subparagraphs 2, 4, 15 and 20;
118. compounds of subparagraphs 2, 4, 15 and 21;
119. compounds of subparagraphs 2, 4, 15 and 22;
120. compounds of subparagraphs 2, 4, 15 and 23;
121. compounds of subparagraphs 2, 4, 15 and 24;
122. compounds of subparagraphs 2, 4, 15 and 25;
123. compounds of subparagraphs 2, 4, 15 and 26;
124. compounds of subparagraphs 2, 4, 16 and 19;
125. compounds of subparagraphs 2, 4, 16 and 20;
126. compounds of subparagraphs 2, 4, 16 and 21;
127. compounds of subparagraphs 2, 4, 16 and 22;
128. compounds of subparagraphs 2, 4, 16 and 23;
129. compounds of subparagraghs 2, 4, 16 and 24;
130. compounds of subparagraphs 2, 4, 16 and 25;
131. compounds of subparagraphs 2, 4, 16 and 26;
132. compounds of subparagraphs 2, 4, 17 and 19;
133. compounds of subparagraphs 2, 4, 17 and 20;
134. compounds of subparagraphs 2, 4, 17 and 21;
135. compounds of subparagraphs 2, 4, 17 and 22;
136. compounds of subparagraphs 2, 4, 17 and 23;
137. compounds of subparagraphs 2, 4, 17 and 24;
138. compounds of subparagraphs 2, 4, 17 and 25;
139. compounds of subparagraphs 2, 4, 17 and 26;
140. compounds of subparagraphs 2, 4, 18 and 19;
141. compounds of subparagraphs 2, 4, 18 and 20;
142. compounds of subparagraphs 2, 4, 18 and 21;
143. compounds of subparagraphs 2, 4, 18 and 22;
144. compounds of subparagraphs 2, 4, 18 and 23;
145. compounds of subparagraphs 2, 4, 18 and 24;
146. compounds of subparagraphs 2, 4, 18 and 25;
147. compounds of subparagraphs 2, 4, 18 and 26;
148. compounds of subparagraphs 2, 4, 27 and 33;
149. compounds of subparagraphs 2, 4, 27 and 34;
150. compounds of subparagraphs 2, 4, 27 and 35;
151. compounds of subparagraphs 2, 4, 27 and 36;
152. compounds of subparagraphs 2, 4, 27 and 37;
153. compounds of subparagraphs 2, 4, 28 and 33;
154. compounds of subparagraphs 2, 4, 28 and 34;
155. compounds of subparagraphs 2, 4, 28 and 35;
156. compounds of subparagraphs 2, 4, 28 and 36;
157. compounds of subparagraphs 2, 4, 28 and 37;
158. compounds of subparagraphs 2, 4, 29 and 33;
159. compounds of subparagraphs 2, 4, 29 and 34;
160. compounds of subparagraphs 2, 4, 29 and 35;
161. compounds of subparagraphs 2, 4, 29 and 36;
162. compounds of subparagraphs 2, 4, 29 and 37;
163. compounds of subparagraphs 2, 4, 30 and 33;
164. compounds of subparagraphs 2, 4, 30 and 34;
165. compounds of subparagraphs 2, 4, 30 and 35;
166. compounds of subparagraphs 2, 4, 30 and 36;
167. compounds of subparagraphs 2, 4, 30 and 37;
168. compounds of subparagraphs 2, 4, 31 and 33;
169. compounds of subparagraphs 2, 4, 31 and 34;
170. compounds of subparagraphs 2, 4, 31 and 35;
171. compounds of subparagraphs 2, 4, 31 and 36;
172. compounds of subparagraphs 2, 4, 31 and 37;
173. compounds of subparagraphs 2, 4, 32 and 33;
174. compounds of subparagraphs 2, 4, 32 and 34;
175. compounds of subparagraphs 2, 4, 32 and 35;
176. compounds of subparagraphs 2, 4, 32 and 36;
177. compounds of subparagraphs 2, 4, 32 and 37;
178. compounds of subparagraphs 3, 4, 38 and 44;
179. compounds of subparagraphs 3, 4, 38 and 45;
180. compounds of subparagraphs 3, 4, 38 and 46;
181. compounds of subparagraphs 3, 4, 39 and 44;
182. compounds of subparagraphs 3, 4, 39 and 45;
183. compounds of subparagraphs 3, 4, 39 and 46;
184. compounds of subparagraphs 3, 4, 40 and 44;
185. compounds of subparagraphs 3, 4, 40 and 45;
186. compounds of subparagraphs 3, 4, 40 and 46;
187. compounds of subparagraphs 3, 4, 41 and 44;
188. compounds of subparagraphs 3, 4, 41 and 45;
189. compounds of subparagraphs 3, 4, 41 and 46;
190. compounds of subparagraphs 3, 4, 42 and 44;
191. compounds of subparagraphs 3, 4, 42 and 45;

192. compounds of subparagraphs 3, 4, 42 and 46;
193. compounds of subparagraphs 3, 4, 43 and 44;
194. compounds of subparagraphs 3, 4, 43 and 45;
195. compounds of subparagraphs 3, 4, 43 and 46;
196. compounds of subparagraphs 3, 4, 38 and 47;
197. compounds of subparagraphs 3, 4, 38 and 48;
198. compounds of subparagraphs 3, 4, 38 and 49;
199. compounds of subparagraphs 3, 4, 39 and 47;
200. compounds of subparagraphs 3, 4, 39 and 48;
201. compounds of subparagraphs 3, 4, 39 and 49;
202. compounds of subparagraphs 3, 4, 40 and 47;
203. compounds of subparagraphs 3, 4, 40 and 48;
204. compounds of subparagraphs 3, 4, 40 and 49;
205. compounds of subparagraphs 3, 4, 41 and 47;
206. compounds of subparagraphs 3, 4, 41 and 48;
207. compounds of subparagraphs 3, 4, 41 and 49;
208. compounds of subparagraphs 3, 4, 42 and 47;
209. compounds of subparagraphs 3, 4, 42 and 48;
210. compounds of subparagraphs 3, 4, 42 and 49;
211. compounds of subparagraphs 3, 4, 43 and 47;
212. compounds of subparagraphs 3, 4, 43 and 48;
213. compounds of subparagraphs 3, 4, 43 and 49;
214. compounds of subparagraphs 3, 4, 44 and 47;
215. compounds of subparagraphs 3, 4, 44 and 48;
216. compounds of subparagraphs 3, 4, 44 and 49;
217. compounds of subparagraphs 3, 4, 45 and 47;
218. compounds of subparagraphs 3, 4, 45 and 48;
219. compounds of subparagraphs 3, 4, 45 and 49;
220. compounds of subparagraphs 3, 4, 46 and 47;
221. compounds of subparagraphs 3, 4, 46 and 48;
222. compounds of subparagraphs 3, 4, 46 and 49;
223. compounds of subparagraphs 3, 4, 38, 44 and 47;
224. compounds of subparagraphs 3, 4, 38, 44 and 48;
225. compounds of subparagraphs 3, 4, 38, 44 and 49;
226. compounds of subparagraphs 3, 4, 38, 44 and 50;
227. compounds of subparagraphs 3, 4, 38, 44 and 51;
228. compounds of subparagraphs 3, 4, 38, 44 and 52;
229. compounds of subparagraphs 3, 4, 38, 45 and 47;
230. compounds of subparagraphs 3, 4, 38, 45 and 48;
231. compounds of subparagraphs 3, 4, 38, 45 and 49;
232. compounds of subparagraphs 3, 4, 38, 45 and 50;
233. compounds of subparagraphs 3, 4, 38, 45 and 51;
234. compounds of subparagraphs 3, 4, 38, 45 and 52;
235. compounds of subparagraphs 3, 4, 38, 46 and 47;
236. compounds of subparagraphs 3, 4, 38, 46 and 48;
237. compounds of subparagraphs 3, 4, 38, 46 and 49;
238. compounds of subparagraphs 3, 4, 38, 46 and 50;
239. compounds of subparagraphs 3, 4, 38, 46 and 51;
240. compounds of subparagraphs 3, 4, 38, 46 and 52;
241. compounds of subparagraphs 3, 4, 39, 44 and 47;
242. compounds of subparagraphs 3, 4, 39, 44 and 48;
243. compounds of subparagraphs 3, 4, 39, 44 and 49;
244. compounds of subparagraphs 3, 4, 39, 44 and 50;
245. compounds of subparagraphs 3, 4, 39, 44 and 51;
246. compounds of subparagraphs 3, 4, 39, 44 and 52;
247. compounds of subparagraphs 3, 4, 39, 45 and 47;
248. compounds of subparagraphs 3, 4, 39, 45 and 48;
249. compounds of subparagraphs 3, 4, 39, 45 and 49;
250. compounds of subparagraphs 3, 4, 39, 45 and 50;
251. compounds of subparagraphs 3, 4, 39, 45 and 51;
252. compounds of subparagraphs 3, 4, 39, 45 and 52;
253. compounds of subparagraphs 3, 4, 39, 46 and 47;
254. compounds of subparagraphs 3, 4, 39, 46 and 48;
255. compounds of subparagraphs 3, 4, 39, 46 and 49;
256. compounds of subparagraphs 3, 4, 39, 46 and 50;
257. compounds of subparagraphs 3, 4, 39, 46 and 51;
258. compounds of subparagraphs 3, 4, 39, 46 and 52;
259. compounds of subparagraphs 3, 4, 40, 44 and 47;
260. compounds of subparagraphs 3, 4, 40, 44 and 48;
261. compounds of subparagraphs 3, 4, 40, 44 and 49;
262. compounds of subparagraphs 3, 4, 40, 44 and 50;
263. compounds of subparagraphs 3, 4, 40, 44 and 51;
264. compounds of subparagraphs 3, 4, 40, 44 and 52;
265. compounds of subparagraphs 3, 4, 40, 45 and 47;
266. compounds of subparagraphs 3, 4, 40, 45 and 48;
267. compounds of subparagraphs 3, 4, 40, 45 and 49;
268. compounds of subparagraphs 3, 4, 40, 45 and 50;
269. compounds of subparagraphs 3, 4, 40, 45 and 51;
270. compounds of subparagraphs 3, 4, 40, 45 and 52;
271. compounds of subparagraphs 3, 4, 40, 46 and 47;
272. compounds of subparagraphs 3, 4, 40, 46 and 48;
273. compounds of subparagraphs 3, 4, 40, 46 and 49;
274. compounds of subparagraphs 3, 4, 40, 46 and 50;
275. compounds of subparagraphs 3, 4, 40, 46 and 51;
276. compounds of subparagraphs 3, 4, 40, 46 and 52;
277. compounds of subparagraphs 3, 4, 41, 44 and 47;
278. compounds of subparagraphs 3, 4, 41, 44 and 48;
279. compounds of subparagraphs 3, 4, 41, 44 and 49;
280. compounds of subparagraphs 3, 4, 41, 44 and 50;
281. compounds of subparagraphs 3, 4, 41, 44 and 51;
282. compounds of subparagraphs 3, 4, 41, 44 and 52;
283. compounds of subparagraphs 3, 4, 41, 45 and 47;
284. compounds of subparagraphs 3, 4, 41, 45 and 48;
285. compounds of subparagraphs 3, 4, 41, 45 and 49;
286. compounds of subparagraphs 3, 4, 41, 45 and 50;
287. compounds of subparagraphs 3, 4, 41, 45 and 51;
288. compounds of subparagraphs 3, 4, 41, 45 and 52;
289. compounds of subparagraphs 3, 4, 41, 46 and 47;
290. compounds of subparagraphs 3, 4, 41, 46 and 48;
291. compounds of subparagraphs 3, 4, 41, 46 and 49;
292. compounds of subparagraphs 3, 4, 41, 46 and 50;
293. compounds of subparagraphs 3, 4, 41, 46 and 51;
294. compounds of subparagraphs 3, 4, 41, 46 and 52;
295. compounds of subparagraphs 3, 4, 42, 44 and 47;
296. compounds of subparagraphs 3, 4, 42, 44 and 48;
297. compounds of subparagraphs 3, 4, 42, 44 and 49;
298. compounds of subparagraphs 3, 4, 42, 44 and 50;
299. compounds of subparagraphs 3, 4, 42, 44 and 51;
300. compounds of subparagraphs 3, 4, 42, 44 and 52;
301. compounds of subparagraphs 3, 4, 42, 45 and 47;
302. compounds of subparagraphs 3, 4, 42, 45 and 48;
303. compounds of subparagraphs 3, 4, 42, 45 and 49;
304. compounds of subparagraphs 3, 4, 42, 45 and 50;
305. compounds of subparagraphs 3, 4, 42, 45 and 51;
306. compounds of subparagraphs 3, 4, 42, 45 and 52;
307. compounds of subparagraphs 3, 4, 42, 46 and 47;
308. compounds of subparagraphs 3, 4, 42, 46 and 48;
309. compounds of subparagraphs 3, 4, 42, 46 and 49;
310. compounds of subparagraphs 3, 4, 42, 46 and 50;
311. compounds of subparagraphs 3, 4, 42, 46 and 51;
312. compounds of subparagraphs 3, 4, 42, 46 and 52;
313. compounds of subparagraphs 3, 4, 43, 44 and 47;
314. compounds of subparagraphs 3, 4, 43, 44 and 48;
315. compounds of subparagraphs 3, 4, 43, 44 and 49;
316. compounds of subparagraphs 3, 4, 43, 44 and 50;
317. compounds of subparagraphs 3, 4, 43, 44 and 51;
318. compounds of subparagraphs 3, 4, 43, 44 and 52;
319. compounds of subparagraphs 3, 4, 43, 45 and 47;
320. compounds of subparagraphs 3, 4, 43, 45 and 48;
321. compounds of subparagraphs 3, 4, 43, 45 and 49;
322. compounds of subparagraphs 3, 4, 43, 45 and 50;
323. compounds of subparagraphs 3, 4, 43, 45 and 51;
324. compounds of subparagraphs 3, 4, 43, 45 and 52;
325. compounds of subparagraphs 3, 4, 43, 46 and 47;
326. compounds of subparagraphs 3, 4, 43, 46 and 48;
327. compounds of subparagraphs 3, 4, 43, 46 and 49;

328. compounds of subparagraphs 3, 4, 43, 46 and 50;
329. compounds of subparagraphs 3, 4, 43, 46 and 51;
330. compounds of subparagraphs 3, 4, 43, 46 and 52;
331. compounds of subparagraphs 3, 5, and 50;
332. compounds of subparagraphs 3, 5 and 51;
333. compounds of subparagraphs 3, 5 and 52;
334. compounds of subparagraphs 3, 6 and 50;
335. compounds of subparagraphs 3, 6 and 51;
336. compounds of subparagraphs 3, 6 and 52;
337. compounds of subparagraphs 3, 7 and 50;
338. compounds of subparagraphs 3, 7 and 51;
339. compounds of subparagraphs 3, 7 and 52;
340. compounds of subparagraphs 3, 5, 53 and 56;
341. compounds of subparagraphs 3, 5, 53 and 57;
342. compounds of subparagraphs 3, 5, 53 and 58;
343. compounds of subparagraphs 3, 5, 53 and 59;
344. compounds of subparagraphs 3, 5, 54 and 56;
345. compounds of subparagraphs 3, 5, 54 and 57;
346. compounds of subparagraphs 3, 5, 54 and 58;
347. compounds of subparagraphs 3, 5, 54 and 59;
348. compounds of subparagraphs 3, 5, 55 and 56;
349. compounds of subparagraphs 3, 5, 55 and 57;
350. compounds of subparagraphs 3, 5, 55 and 58;
351. compounds of subparagraphs 3, 5, 55 and 59;
352. compounds of subparagraphs 3, 6, 53 and 56;
353. compounds of subparagraphs 3, 6, 53 and 57;
354. compounds of subparagraphs 3, 6, 53 and 58;
355. compounds of subparagraphs 3, 6, 53 and 59;
356. compounds of subparagraphs 3, 6, 54 and 56;
357. compounds of subparagraphs 3, 6, 54 and 57;
358. compounds of subparagraphs 3, 6, 54 and 58;
359. compounds of subparagraphs 3, 6, 54 and 59;
360. compounds of subparagraphs 3, 6, 55 and 56;
361. compounds of subparagraphs 3, 6, 55 and 57;
362. compounds of subparagraphs 3, 6, 55 and 58;
363. compounds of subparagraphs 3, 6, 55 and 59;
364. compounds of subparagraphs 3, 7, 53 and 56;
365. compounds of subparagraphs 3, 7, 53 and 57;
366. compounds of subparagraphs 3, 7, 53 and 58;
367. compounds of subparagraphs 3, 7, 53 and 59;
368. compounds of subparagraphs 3, 7, 54 and 56;
369. compounds of subparagraphs 3, 7, 54 and 57;
370. compounds of subparagraphs 3, 7, 54 and 58;
371. compounds of subparagraphs 3, 7, 54 and 59;
372. compounds of subparagraphs 3, 7, 55 and 56;
373. compounds of subparagraphs 3, 7, 55 and 57;
374. compounds of subparagraphs 3, 7, 55 and 58;
375. compounds of subparagraphs 3, 7, 55 and 59;
376. compounds of subparagraphs 2, 4 and 8;
377. compounds of subparagraphs 2, 4 and 9;
378. compounds of subparagraphs 2, 4 and 10;
379. compounds of subparagraphs 2, 4 and 11;
380. compounds of subparagraphs 2, 4 and 12;
381. compounds of subparagraphs 2, 4 and 13;
382. compounds of subparagraphs 2, 4 and 14;
383. compounds of subparagraphs 2, 4 and 15;
384. compounds of subparagraphs 2, 4 and 16;
385. compounds of subparagraphs 2, 4 and 17;
386. compounds of subparagraphs 2, 4 and 18;
387. compounds of subparagraphs 2, 4 and 19;
388. compounds of subparagraphs 2, 4 and 20;
389. compounds of subparagraphs 2, 4 and 21;
390. compounds of subparagraphs 2, 4 and 22;
391. compounds of subparagraphs 2, 4 and 23;
392. compounds of subparagraphs 2, 4 and 24;
393. compounds of subparagraphs 2, 4 and 25;
394. compounds of subparagraphs 2, 4 and 26;
395. compounds of subparagraphs 3, 4 and 38;
396. compounds of subparagraphs 3, 4 and 39;
397. compounds of subparagraphs 3, 4 and 40;
398. compounds of subparagraphs 3, 4 and 41;
399. compounds of subparagraphs 3, 4 and 42;
400. compounds of subparagraphs 3, 4 and 43;
401. compounds of subparagraphs 3, 4 and 44;
402. compounds of subparagraphs 3, 4 and 45;
403. compounds of subparagraphs 3, 4 and 46;
404. compounds of subparagraphs 3, 4 and 47;
405. compounds of subparagraphs 3, 4 and 48;
406. compounds of subparagraphs 3, 4 and 49;
407. compounds of subparagraphs 3, 5 and 53;
408. compounds of subparagraphs 3, 5 and 54;
409. compounds of subparagraphs 3, 5 and 56;
410. compounds of subparagraphs 3, 5 and 57;
411. compounds of subparagraphs 3, 5 and 58;
412. compounds of subparagraphs 3, 5 and 59;
413. compounds of subparagraphs 3, 6 and 53;
414. compounds of subparagraphs 3, 6 and 54;
415. compounds of subparagraphs 3, 6 and 55;
416. compounds of subparagraphs 3, 6 and 56;
417. compounds of subparagraphs 3, 6 and 57;
418. compounds of subparagraphs 3, 6 and 58;
419. compounds of subparagraphs 3, 6 and 59;
420. compounds of subparagraphs 3, 7 and 53;
421. compounds of subparagraphs 3, 7 and 54;
422. compounds of subparagraphs 3, 7 and 55;
423. compounds of subparagraphs 3, 7 and 56;
424. compounds of subparagraphs 3, 7 and 57;
425. compounds of subparagraphs 3, 7 and 58;
426. compounds of subparagraphs 3, 7 and 59;

Particularly preferred classes of compounds are the following

Compounds of subparagraphs 2 and 4;
Compounds of subparagraphs 3 and 4;
Compounds of subparagraphs 3 and 5;
Compounds of subparagraphs 3 and 6.

It is believed that the compounds useful in this invention are clearly described by the above generic formula. In order to assure that those skilled in the art understand the invention, however, the following exemplary compounds, which are not intended to delineate the bounds of the invention, are named.

2,3,5,6-tetrachloro-2',4',6'-trinitrodiphenylamine
2',4'-dinitro-2,4,6-trifluoro-6'-trifluoromethyldiphenylamine
4-bromo-3,5-dichloro-2',4',6'-trinitrodiphenylamine
2,3,4,5-tetrabromo-2',4',6'-trinitrodiphenylamine
2,5-dibromo-4-trifluoromethyl-2',4',6'-trinitrodiphenylamine
4-chloro-3,5-dibromo-2',4',6'-trinitrodiphenylamine
2,3,5-tribromo-6'-trifluoromethyl-2',4,4'-trinitrodiphenylamine
2,6-dinitro-2',3',4',5',6'-pentabromo-4-trifluoromethyldiphenylamine
2,6-dibromo-3,5-dichloro-2',4'-dinitro-6'-trifluoromethyldiphenylamine
2,3,5,6-tetrabromo-2',4',6'-trinitrodiphenylamine
2,3,5,6-tetrachloro-4-trifluoromethyl-2',4',6'-trinitrodiphenylamine
2,5-dichloro-2',4,4'-trinitro-6'-trifluoromethyldiphenylamine
2,5-dichloro-4-cyano-2',4'-dinitro-6'-trifluoromethyldiphenylamine
3,4,6-trichloro-2-methyl-2',4'-dinitro-6'-trifluoromethyldiphenylamine 4,5,6-tribromo-2-methyl-2',4'-dinitro-6'-trifluoromethyldiphenylamine
4,6-dibromo-3-chloro-2-methyl-2',4'-dinitro-6'-trifluoromethyldiphenylamine
3-bromo-2,4-difluoro-6-methyl-2',4'-dinitro-6'-trifluoromethyldiphenylamine.
3,4-dichloro-2-fluoro-6-methyl-2',4'-dinitro-6'-trifluoromethyldiphenylamine
2,3-dibromo-4-chloro-6-methyl-2',4'-dinitro-6'-trifluoromethyldiphenylamine
2,3-dibromo-4-fluoro-6-methyl-2',4'-dinitro-6'-trifluoromethyldiphenylamine
2,4-dichloro-5-fluoro-6-methyl-2',4'-dinitro-6'-trifluoromethyldiphenylamine
3,4-dibromo-6-chloro-2-methyl-2',4'-dinitro-6'-trifluoromethyldiphenylamine
2,3,4,5-tetrachloro-6-methyl-2',4'-dinitro-6'-trifluoromethyldiphenylamine
2,3,4,5-tetrabromo-6-methyl-2',4'-dinitro-6'-trifluoromethyldiphenylamine
3-bromo-4-chloro-6-fluoro-2-methyl-2',4'-dinitro-6'-trifluoromethyldiphenylamine
3-chloro-4,6-difluoro-2-methyl-2',4'-dinitro-6'-trifluoromethyldiphenylamine
2,5-dichloro-2',4'-dinitro-4,6'bis(trifluoromethyl)diphenylamine
2,4-dichloro-6-fluoro-2',4,4'-trinitro-6'-trifluoromethyldiphenylamine
2-chloro-4-cyano-6-fluoro-2',4'-dinitro-6'-trifluoromethyldiphenylamine
2-chloro-6-bromo-2',4'-dinitro-4,6'-bis(trifluoromethyl)diphenylamine
3,5-dibromo-2',4,4'-trinitro-6'-trifluoromethyldiphenylamine
3,5-dibromo-4-cyano-2',4'-dinitro-6'-trifluoromethyldiphenylamine
3,5-dibromo-2',4'-dinitro-4,6'-bis(trifluoromethyl)diphenylamine
2,6-difluoro-2',4,4'-trinitro-6'-trifluoromethyldiphenylamine
4-cyano-2,6-difluoro-2',4'-dinitro-6'-trifluoromethyldiphenylamine
2,6-dibromo-3,5-dichloro-2',4,4'-trinitro-6'-trifluoromethyldiphenylamine
2,6-dibromo-4-cyano-3-fluoro-2',4'-dinitro-6'-trifluoromethyldiphenylamine
2,6-dibromo-3-chloro-2',4'-dinitro-4,6'-bis(trifluoromethyl)diphenylamine
3,5-dibromo-2-chloro-2',4'-dinitro-6'-trifluoromethyldiphenylamine
2-bromo-6-fluoro-2',4,4'-trinitro-6'-trifluoromethyldiphenylamine
2,3,5,6-tetrabromo-4-cyano-2',4'-dinitro-6'-trifluoromethyldiphenylamine
3-bromo-4-chloro-2',4'-dinitro-6'-trifluoromethyldiphenylamine
3-chloro-2',4,4'-trinitro-6'-trifluoromethyldiphenylamine
2,3-dichloro-2',4'-dinitro-6'-trifluoromethyldiphenylamine
2-bromo-2',4'-dinitro-4,6'-bis(trifluoromethyl)diphenylamine
2,3-dibromo-5-chloro-2',4'-dinitro-6'-trifluoromethyldiphenylamine
2-bromo-4-cyano-6-fluoro-2',4'-dinitro-6'-trifluoromethyldiphenylamine
2-bromo-5-chloro-2',4'-dinitro-6'-trifluoromethyldiphenylamine
4-cyano-3-fluoro-2',4'-dinitro-6'-trifluoromethyldiphenylamine
2',4'-dinitro-4,6'-bis(trifluoromethyl)diphenylamine
2,3,5,6-tetrabromo-2',4,4'-trinitro-6'-trifluoromethyldiphenylamine
4-chloro-2,6-difluoro-2',4'-dinitro-6'-trifluoromethyldiphenylamine
3-chloro-4-cyano-2',4'-dinitro-6'-trifluoromethyldiphenylamine
4-chloro-2-fluoro-2',4'-dinitro-6'-trifluoromethyldiphenylamine
4-bromo-2-chloro-6-fluoro-2',4'-dinitro-6'-trifluoromethyldiphenylamine
3-chloro-2',4'-dinitro-4,6'-bis(trifluoromethyl)diphenylamine
4-bromo-2,5-dichloro-2',4'-dinitro-6'-trifluoromethyldiphenylamine
2-bromo-4-chloro-2',4'-dinitro-6'-trifluoromethyldiphenylamine
2-bromo-4-cyano-2',4'-dinitro-6'-trifluoromethyldiphenylamine
2-fluoro-2',4,4'-trinitro-6'-trifluoromethyldiphenylamine
3-bromo-4-chloro-5-fluoro-2',4'-dinitro-6'-trifluoromethyldiphenylamine
2,3,5,6-tetrabromo-2',4'-dinitro-4,6'-bis(trifluoromethyl)diphenylamine
2-bromo-2',4'-dinitro-4,6'-bis(trifluoromethyl)diphenylamine
4-bromo-3,5-dichloro-2',4'-dinitro-6'-trifluoromethyldiphenylamine
2,6-dichloro-4-fluoro-2',4'-dinitro-6'-trifluoromethyldiphenylamine
2,5-dibromo-4-fluoro-2',4'-dinitro-6'-trifluoromethyldiphenylamine
2-bromo-2',4,4'-trinitro-6'-trifluoromethyldiphenylamine
4-cyano-2-fluoro-2',4'-dinitro-6'-trifluoromethyldiphenylamine
3,5-dibromo-4-fluoro-2',4'-dinitro-6'-trifluoromethyldiphenylamine
2,3,4,5,6-pentafluoro-2',4'-dinitro-6'-trifluoromethyldiphenylamine
3,4-dichloro-2,6-difluoro-2',4'-dinitro-6'-trifluoromethyldiphenylamine
2,3,4,6-tetrabromo-2',4'-dinitro-6'-trifluoromethyldiphenylamine
2,5-dichloro-3-fluoro-2',4'-dinitro-6'-trifluoromethyldiphenylamine
2,3,4,5-tetrachloro-2',4'-dinitro-6'-trifluoromethyldiphenylamine
2,6-difluoro-4-iodo-2',4'-dinitro-6'-trifluoromethyldiphenylamine
3,5-dichloro-4-iodo-2',4'-dinitro-6'-trifluoromethyldiphenylamine
2,3-dibromo-6-chloro-4-iodo-2',4'-dinitro-6'-trifluoromethyldiphenylamine
2,5-dibromo-4-iodo-2',4'-dinitro-6'-trifluoromethyldiphenylamine
3,5-dichloro-2,6-difluoro-4-iodo-2',4'-dinitro-6'-trifluoromethyldiphenylamine
2-fluoro-4-iodo-2',4'-dinitro-6'-trifluoromethyldiphenylamine
3-bromo-4-iodo-2',4'-dinitro-6'-trifluoromethyldiphenylamine
2-chloro-5-fluoro-4-iodo-2',4'-dinitro-6'-trifluoromethyldiphenylamine
2,3,5,6-tetrabromo-2',4',6'-trinitrodiphenylamine 4-chloro-2,3,5,6-tetrabromo-2',4',6'-trinitrodiphenylamine
2,5-dibromo-4-chloro-2',4',6'-trinitrodiphenylamine
3,5-dibromo-2,4,6-trichloro-2',4',6'-trinitrodiphenylamine
3-bromo-4,5-dichloro-2',4',6'-trinitrodiphenylamine
2,3,6-trichloro-4-fluoro-2',4',6'-trinitrodiphenylamine
2,4-dichloro-5-fluoro-2',4',6'-trinitrodiphenylamine
2,6-dibromo-4-fluoro-2',4',6'-trinitrodiphenylamine
2,3,5,6-tetrabromo-4-fluoro-2',4',6'-trinitrodiphenylamine
2,4-dibromo-6-fluoro-2',4',6'-trinitrodiphenylamine
2,3,5,6-tetrachloro-4-fluoro-2',4',6'-trinitrodiphenylamine
2,3,4,6-tetrabromo-2',4',6'-trinitrodiphenylamine
4-bromo-2,3,6-trichloro-2',4',6'-trinitrodiphenylamine
4-fluoro-2,3,5,6-tetrachloro-2',4',6'-trinitrodiphenylamine
4-bromo-2,3,5,6-tetrachloro-2',4',6'-trinitrodiphenylamine
2,5-dibromo-4-iodo-2',4',6'-trinitrodiphenylamine
2,6-dibromo-4-iodo-2',4',6'-trinitrodiphenylamine
2,3,5-trichloro-4-iodo-2',4',6'-trinitrodiphenylamine
2,3,5,6-tetrachloro-4-iodo-2',4',6'-trinitrodiphenylamine
2-chloro-4-iodo-2',4'6,6'-tetranitrodiphenylamine
2,4-dichloro-2',4',6,6'-tetranitrodiphenylamine
2,4,5-tribromo-2',4',6,6'-tetranitrodiphenylamine
2-chloro-2',4',6,6'-tetranitro-4-trifluoromethyldiphenylamine
4-cyano-2-chloro-2',4',6,6'-tetranitrodiphenylamine
2,6-dichloro-4-cyano-2',4',6'-trinitrodiphenylamine
2,3,5-tribromo-4-cyano-2',4',6'-trinitrodiphenylamine
5-bromo-2-chloro-4-cyano-2',4',6'-trinitrodiphenylamine
6-bromo-2-chloro-4-cyano-5-fluoro-2',4',6'-trinitrodiphenylamine
2,6-dibromo-4-cyano-2',4',6'-trinitrodiphenylamine
2,3,6-trichloro-4-cyano-2',4',6'-trinitrodiphenylamine
4-cyano-2,5-dichloro-2',4',6'-trinitrodiphenylamine
2,6-dichloro-2',4,4',6'-tetranitrodiphenylamine
5-bromo-2-chloro-2',4,4',6'-tetranitrodiphenylamine
5-chloro-2,6-dibromo-2',4,4',6'-tetranitrodiphenylamine
2,6-dibromo-2',4,4',6'-tetranitrodiphenylamine
2,6-dichloro-2',4,4',6'-tetranitrodiphenylamine
2,3,6-trichloro-2',4,4',6'-tetranitrodiphenylamine
2,5-dibromo-2',4,4',6'-tetranitrodiphenylamine
2,3,5-tribromo-2',4,4',6'-tetranitrodiphenylamine
5-fluoro-2,6-dichloro-2',4',6'-trinitrodiphenylamine
2,6-dibromo-2',4',6'-trinitro-4-trifluoromethyldiphenylamine
2,3,5-tribromo-2',4',6'-trinitro-4-trifluoromethyldiphenylamine
2,6-dichloro-2',4',6'-trinitro-4-trifluoromethyldiphenylamine
5-bromo-2-chloro-2',4',6'-trinitro-4-trifluoromethyldiphenylamine
2,3,6-trichloro-2',4',6'-trinitro-4-trifluoromethyldiphenylamine
2-chloro-6-bromo-2',4',6'-trinitro-4-trifluoromethyldiphenylamine
2,6-dibromo-2',4',6'-trinitro-4-trifluoromethyldiphenylamine
2,5-dibromo-3-fluoro-2',4',6'-trinitrodiphenylamine
2,3,5,6-tetrachloro-2',4',6'-trinitrodiphenylamine
2,3,5-tribromo-2',4',6'-trinitrodiphenylamine
5-bromo-2,4-dichloro-2',4',6'-trinitrodiphenylamine
3,5-dichloro-2,6-dibromo-2',4',6'-trinitrodiphenylamine
2,3,5-trichloro-2',4',6,6'-tetranitrodiphenylamine
2,3,4,5,6-pentachloro-N-methyl-2',4',6'-trinitrodiphenylamine
2,3,4,5,6-pentabromo-N-ethyl-2',4',6'-trinitrodiphenylamine
2,3,4,5,6-pentafluoro-2',4',6'-trinitro-N-propyldiphenylamine
N-methyl-2,3,6-trichloro-4-fluoro-2',4',6'-trinitrodiphenylamine
2,3,5-tribromo-N-ethyl-2',4',6'-trinitrodiphenylamine
N-ethyl-2,6-dibromo-4-fluoro-2',4',6'-trinitrodiphenylamine
3,4,5-tribromo-2',4',6'-trinitro-N-propyldiphenylamine
3-fluoro-N-ethyl-4,6-dichloro-2',4',6'-trinitrodiphenylamine
2,4-dibromo-N-ethyl-6-fluoro-2',4',6'-trinitrodiphenylamine
3,5-dichloro-2,6-dibromo-N-methyl-2',4',6'-trinitrodiphenylamine
4-bromo-2,6-dichloro-N-methyl-2',4',6'-trinitrodiphenylamine
N-propyl-3,4,5-trichloro-2',4',6'-trinitrodiphenylamine
4-fluoro-2,6-dibromo-N-methyl-2',4',6'-trinitrodiphenylamine
3,5-dibromo-2-chloro-2',4',6'-trinitro-N-propyldiphenylamine
2,3,6-trichloro-4-fluoro-N-methyl-2',4',6'-trinitrodiphenylamine
N-ethyl-2,3,4,5,6-pentachloro-2',4',6'-trinitrodiphenylamine
2,3,4,5-tetrachloro-N-ethyl-2',4',6'-trinitrodiphenylamine
2,4-dibromo-6-fluoro-2',4',6'-trinitro-N-propyldiphenylamine
2,6-dibromo-4-fluoro-N-methyl-2',4',6'-trinitrodiphenylamine
3,4,5-tribromo-N-ethyl-2',4',6'-trinitrodiphenylamine
4-bromo-2,6-dichloro-2',4',6'-trinitro-N-propyldiphenylamine
2,3,4,5,6-pentabromo-2',4',6'-trinitro-N-propyldiphenylamine
2,3,5,6-tetrachloro-N-propyl-2',4',6'-trinitrodiphenylamine
4,6-dichloro-N-ethyl-2-fluoro-2',4',6'-trinitrodiphenylamine
3,5-dibromo-2-chloro-N-ethyl-2',4',6'-trinitrodiphenylamine
2,3,5-tribromo-2',4',6'-trinitro-N-propyldiphenylamine
2,3,5,6-tetrabromo-N-methyl-2',4',6'-trinitrodiphenylamine
4-bromo-2,6-dichloro-N-ethyl-2',4',6'-trinitrodiphenylamine
3-fluoro-4,6-dichloro-2',4',6'-trinitro-N-propyldiphenylamine
3,4,5-trichloro-N-methyl-2',4',6'-trinitrodiphenylamine
2-bromo-6-fluoro-4-methyl-2',4'-dinitro-6'-trifluoromethyldiphenylamine
2,4-dichloro-6-methyl-2',4'-dinitro-6'-trifluoromethyldiphenylamine
2,4-dichloro-3-methyl-2',4'-dinitro-6'-trifluoromethyldiphenylamine 2,4-dibromo-5-methyl-2',4'-dinitro-6'-trifluoromethyldiphenylamine
2,6-dichloro-3-methyl-2',4'-dinitro-6'-trifluoromethyldiphenylamine
2-bromo-6-fluoro-5-methyl-2',4'-dinitro-6'-trifluoromethyldiphenylamine
6-chloro-2-fluoro-3-methyl-2',4'-dinitro-6'-trifluoromethyldiphenylamine
2,4-difluoro-6-methyl-2',4'-dinitro-6'-trifluoromethyldiphenylamine
2,4-dibromo-6-methyl-2',4'-dinitro-6'-trifluoromethyldiphenylamine
4-chloro-2-fluoro-6-methyl-2',4'-dinitro-6'-trifluoromethyldiphenylamine
2-bromo-4-chloro-6-methyl-2',4'-dinitro-6'-trifluoromethyldiphenylamine
2-chloro-6-fluoro-4-methyl-2',4'-dinitro-6'-trifluoromethyldiphenylamine
2,6-dibromo-4-methyl-2',4'-dinitro-6'-trifluoromethyldiphenylamine
2-bromo-6-chloro-4-methyl-2',4'-dinitro-6'-trifluoromethyldiphenylamine
2,4-difluoro-3-methyl-2',4'-dinitro-6'-trifluoromethyldiphenylamine
2,6-dibromo-3-methyl-2',4'-dinitro-6'-trifluoromethyldiphenylamine
2-bromo-4-chloro-5-methyl-2',4'-dinitro-6'-trifluoromethyldiphenylamine
2-bromo-4-fluoro-5-methyl-2',4'-dinitro-6'-trifluoromethyldiphenylamine
2,6-difluoro-4-methyl-2',4'-dinitro-6'-trifluoromethylphenylamine
2-bromo-4-fluoro-6-methyl-2',4'-dinitro-6'-trifluoromethyldiphenylamine
2,4-dichloro-5-methyl-2',4'-dinitro-6'-trifluoromethyldiphenylamine
2,6-difluoro-3-methyl-2',4'-dinitro-6'-trifluoromethyldiphenylamine
2-chloro-4-fluoro-3-methyl-2',4'-dinitro-6'-trifluoromethyldiphenylamine
2,4-dibromo-6-fluoro-5-methyl-2',4'-dinitro-6'-trifluoromethyldiphenylamine
2,4,6-trichloro-3-methyl-2',4'-dinitro-6'-trifluoromethyldiphenylamine
4-bromo-2-fluoro-3-methyl-2',4'-dinitro-6'-trifluoromethyldiphenylamine
2-bromo-6-chloro-3-methyl-2',4'-dinitro-6'-trifluoromethyldiphenylamine
2-bromo-6-chloro-3-methyl-2',4'-dinitro-6'-trifluoromethyldiphenylamine
2,4,6-tribromo-3-methyl-2',4'-dinitro-6'-trifluoromethyldiphenylamine
6-bromo-4-chloro-2-fluoro-3-methyl-2',4'-dinitro-6'-trifluoromethyldiphenylamine
4,6-dichloro-2-fluoro-3-methyl-2',4'-dinitro-6'-trifluoromethyldiphenylamine
4,6-dibromo-2-chloro-3-methyl-2',4'-dinitro-6'-trifluoromethyldiphenylamine
2,3,6-trichloro-4-methyl-2',4'-dinitro-6'-trifluoromethyldiphenylamine
2,3,6-tribromo-4-methyl-2',4'-dinitro-6'-trifluoromethyldiphenylamine
3-chloro-2,6-difluoro-4-methyl-2',4'-dinitro-6'-trifluoromethyldiphenylamine
2,6-dichloro-4-methyl-2',4'-dinitro-6'-trifluoromethyldiphenylamine
2,3-dichloro-6-fluoro-4-methyl-2',4'-dinitro-6'-trifluoromethyldiphenylamine
2,3,6-tribromo-5-chloro-4-methyl-2',4'-dinitro-6'-trifluoromethyldiphenylamine
3-bromo-2,6-difluoro-4-methyl-2',4'-dinitro-6'-trifluoromethyldiphenylamine
2,3,5,6-tetrabromo-4-methyl-2',4'-dinitro-6'-trifluoromethyldiphenylamine
3,5-dichloro-2,6-difluoro-4-methyl-2',4'-dinitro-6'-trifluoromethyldiphenylamine
2,4,5-trichloro-3-methyl-2',4'-dinitro-6'-trifluoromethyldiphenylamine
5-chloro-2,4-difluoro-3-methyl-2',4'-dinitro-6'-trifluoromethyldiphenylamine
2,3,4-tribromo-5-methyl-2',4'-dinitro-6'-trifluoromethyldiphenylamine
2,3,5,6-tetrachloro-4-methyl-2',4'-dinitro-6'-trifluoromethyldiphenylamine
2,6-dibromo-3-fluoro-5-methyl-2',4'-dinitro-6'-trifluoromethyldiphenylamine
2-bromo-3,4-dichloro-5-methyl-2',4'-dinitro-6'-trifluoromethyldiphenylamine
2,5-dichloro-4-fluoro-3-methyl-2',4'-dinitro-6'-trifluoromethyldiphenylamine
4,5-dibromo-2-fluoro-3-methyl-2',4'-dinitro-6'-trifluoromethyldiphenylamine
3-bromo-2,6-difluoro-5-methyl-2',4'-dinitro-6'-trifluoromethyldiphenylamine
2,3,6-trichloro-5-methyl-2',4'-dinitro-6'-trifluoromethyldiphenylamine
3-bromo-2,4-dichloro-5-methyl-2',4'-dinitro-6'-trifluoromethyldiphenylamine
3-bromo-5-chloro-2,6-difluoro-4-methyl-2',4'-dinitro-6'-trifluoromethyldiphenylamine
2,3,4-tribromo-6-fluoro-5-methyl-2',4'-dinitro-6'-trifluoromethyldiphenylamine
2,4-dibromo-2',4'-dinitro-5,6'-bis(trifluoromethyl)diphenylamine
2-bromo-6-chloro-2',4'-dinitro-4,6'-bis(trifluoromethyl)diphenylamine
2,4-dibromo-2',4'-dinitro-6,6'-bis(trifluoromethyl)diphenylamine
4-chloro-2-bromo-2',4'-dinitro-6,6'-bis(trifluoromethyl)diphenylamine
2,4-dichloro-2',4'-dinitro-3,6'-bis(trifluoromethyl)diphenylamine
2,6-dibromo-2',4'-dinitro-3,6'-bis(trifluoromethyl)diphenylamine
2,4-dichloro-2',4'-dinitro-5,6'-bis(trifluoromethyl)diphenylamine
2-bromo-4-chloro-2',4'-dinitro-6,6'-bis(trifluoromethyl)diphenylamine
2-chloro-4-bromo-2',4'-dinitro-3,6'-bis(trifluoromethyl)diphenylamine
2-bromo-6-chloro-2',4'-dinitro-3,6'-bis(trifluoromethyl)diphenylamine
2,4,6-trichloro-2',4'-dinitro-3,6'-bis(trifluoromethyl)diphenylamine
2,4-dibromo-2',4'-dinitro-3,6'-bis(trifluoromethyl)diphenylamine
2,4,6-tribromo-2',4'-dinitro-3,6'-bistrifluoromethyl)diphenylamine
4,6-dibromo-2-chloro-2',4'-dinitro-3,6'-bis(trifluoromethyl)diphenylamine
2,4,5,6-tetrachloro-3-methyl-2',4'-dinitro-6'-trifluoromethyldiphenylamine
2,4,6-tribromo-3-chloro-5-methyl-2',4'-dinitro-6'-trifluoromethyldiphenylamine
2-bromo-3,4-dichloro-6-fluoro-5-methyl-2',4'-dinitro-6'trifluoromethyldiphenylamine 2,3,4-trichloro-6-fluoro-5-methyl-2',4'-dinitro-6'-trifluoromethyldiphenylamine
3,4-dibromo-2,6-dichloro-5-methyl-2',4'-dinitro-6'-trifluoromethyldiphenylamine
2,6-dichloro-2',4'-dinitro-4,6'-bis(trifluoromethyl)diphenylamine
2,4-dichloro-2',4'-dinitro-6,6'-bis(trifluoromethyl)diphenylamine
2-bromo-4-chloro-2',4'-dinitro-6,6'-bis(trifluoromethyl)diphenylamine
2,4-dichloro-2',4'-dinitro-3,6'-bis(trifluoromethyl)diphenylamine
2,6-dibromo-2',4'-dinitro-4,6'-bis(trifluoromethyl)diphenylamine
2-chloro-6-bromo-2',4'-dinitro-4,6'-bis(trifluoromethyl)diphenylamine
2,6-dichloro-2',4'-dinitro-3,6'-bis(trifluoromethyl)diphenylamine
2-bromo-4-chloro-2',4'-dinitro-5,6'-bis(trifluoromethyl)diphenylamine
2,6-dichloro-2',4'-dinitro-3,6'-bis(trifluoromethyl)diphenylamine
4,6-dichloro-2-bromo-2',4'-dinitro-3,6'-bis(trifluoromethyl)diphenylamine
6-bromo-4-chloro-2',4'-dinitro-3,6'-bis(trifluoromethyl)diphenylamine
4,6-dichloro-2',4'-dinitro-3,6'-bis(trifluoromethyl)diphenylamine
2,3,6-trichloro-2',4'-dinitro-4,6'-bis(trifluoromethyl)diphenylamine
2,4,5-trichloro-2',4'-dinitro-3,6'-bis(trifluoromethyl)diphenylamine
3-chloro-2,6-dibromo-2',4'-dinitro-4,6'-bis(trifluoromethyl)diphenylamine
5-chloro-2,4-dibromo-2',4'-dinitro-3,6'-bis(trifluoromethyl)diphenylamine
2,3-dichloro-6-bromo-2',4'-dinitro-4,6'-bis(trifluoromethyl)diphenylamine
2,3,6-tribromo-2',4'-dinitro-4,6'-bis(trifluoromethyl)diphenylamine
3-bromo-2,4-dichloro-2',4'-dinitro-5,6'-bis(trifluoromethyl)diphenylamine
2,3,6-tribromo-5-chloro-2',4'-dinitro-4,6'-bis(trifluoromethyl)diphenylamine
2,3,4-tribromo-2',4'-dinitro-5,6'-bis(trifluoromethyl)diphenylamine
2,3,5,6-tetrabromo-2',4'-dinitro-4,6'-bis(trifluoromethyl)diphenylamine
2,3,6-trichloro-2',4'-dinitro-5,6'-bis(trifluoromethyl)diphenylamine
3-bromo-2,6-dichloro-2',4'-dinitro-4,6'-bis(trifluoromethyl)diphenylamine
2-bromo-3,4-dichloro-2',4'-dinitro-5,6'-bis(trifluoromethyl)diphenylamine
2,5-dichloro-4-bromo-2',4'-dinitro-3,6'-bis(trifluoromethyl)diphenylamine
2,3,4-tribromo-2',4'-dinitro-5,6'-bis(trifluoromethyl)diphenylamine
3,5-dichloro-2,6-dibromo-2',4'-dinitro-4,6'-bis(trifluoromethyl)diphenylamine
4,5-dibromo-2-chloro-2',4'-dinitro-3,6'-bis(trifluoromethyl)diphenylamine
2,3,4,6-tetrachloro-2',4'-dinitro-5,6'-bis(trifluoromethyl)diphenylamine
2,3,5,6-tetrachloro-2',4'-dinitro-4,6'-bis(trifluoromethyl)diphenylamine
2,4,6-tribromo-3-chloro-2',4'-dinitro-5,6'-bis(trifluoromethyl)diphenylamine
2-bromo-3,4-dichloro-2',4'-dinitro-5,6'-bis(trifluoromethyl)diphenylamine
2,3,4-trichloro-2',4'-dinitro-5,6'-bis(trifluoromethyl)diphenylamine
3,4-dibromo-2,6-dichloro-2',4'-dinitro-5,6'-bis(trifluoromethyl)diphenylamine
2,5-dichloro-2',4',6'-trinitro-3-trifluoromethyldiphenylamine
4,6-dichloro-2',4',6'-trinitro-3-trifluoromethyldiphenylamine
4,6-dibromo-2',4',6'-trinitro-3-trifluoromethyldiphenylamine
2,5-dibromo-2',4',6'-trinitro-3-trifluoromethyldiphenylamine
2,6-dibromo-4-chloro-2',4',6'-trinitro-3-trifluoromethyldiphenylamine
2,4,6-trichloro-2',4',6'-trinitro-3-trifluoromethyldiphenylamine
2,4,6-tribromo-2',4',6'-trinitro-3-trifluoromethyldiphenylamine
4,6-dibromo-2-chloro-2',4',6'-trinitro-3-trifluoromethyldiphenylamine
2,6-dichloro-4-bromo-2',4',6'-trinitro-3-trifluoromethyldiphenylamine
2,5-dibromo-2',4',6'-trinitro-3-trifluoromethyldiphenylamine
2,5,6-tribromo-2',4',6'-trinitro-3-trifluoromethyldiphenylamine
4,6-dibromo-2-chloro-2',4',6'-trinitro-3-trifluoromethyldiphenylamine
2,6-dichloro-5-bromo-2',4',6'-trinitro-3-trifluoromethyldiphenylamine
4-bromo-2,5-dichloro-2',4',6'-trinitro-3-trifluoromethyldiphenylamine
6-bromo-4-chloro-2',4',6'-trinitro-3-trifluoromethyldiphenylamine
2,4,5,6-tetrachloro-2',4',6'-trinitro-3-trifluoromethyldiphenylamine
2,4,5,6-tetrabromo-2',4',6'-trinitro-3-trifluoromethyldiphenylamine
4,5-dibromo-2,6-dichloro-2',4',6'-trinitro-3-trifluoromethyldiphenylamine
2-bromo-4,5,6-trichloro-2',4',6'-trinitro-3-trifluoromethyldiphenylamine
4,6-dichloro-5-bromo-2',4',6'-trinitro-3-trifluoromethyldiphenylamine
2,6-dibromo-4,5-dichloro-2',4',6'-trinitro-3-trifluoromethyldiphenylamine
4,5,6-tribromo-2-chloro-2',4',6'-trinitro-3-trifluoromethyldiphenylamine
4,5,6-tribromo-2',4'-dinitro-2,6'-bis(trifluoromethyl)diphenylamine
4,6-dibromo-3-chloro-2',4'-dinitro-2,6'-bis(trifluoromethyl)diphenylamine
4,5-dichloro-6-bromo-2',4'-dinitro-2,6'-bis(trifluoromethyl)diphenylamine
5,6-dibromo-4-chloro-2',4'-dinitro-2,6'-bis(trifluoromethyl)diphenylamine
4,6-dichloro-3-bromo-2',4'-dinitro-2,6'-bis(trifluoromethyl)diphenylamine
3,4-dibromo-6-chloro-2',4'-dinitro-2,6'-bis(trifluoromethyl)diphenylamine
3,4,5,6-tetrachloro-2',4'-dinitro-2,6'-bis(trifluoromethyl)diphenylamine
3,4,5,6-tetrabromo-2',4'-dinitro-2,6'-bis(trifluoromethyl)diphenylamine
3-chloro-4,6-dibromo-2',4'-dinitro-2,6'-bis(trifluoromethyl)diphenylamine 2,4-dichloro-3,5-dimethyl-2',4'-dinitro-6'-trifluoromethyldiphenylamine
4-bromo-2-fluoro-3,5-dimethyl-2',4'-dinitro-6'-trifluoromethyldiphenylamine
2,4,6-tribromo-3,5-dimethyl-2',4'-dinitro-6'-trifluoromethyldiphenylamine
2-chloro-4,6-difluoro-3,5-dimethyl-2',4'-dinitro-6'-trifluoromethyldiphenylamine
2-bromo-4-chloro-3,5-dimethyl-2',4'-dinitro-6'-trifluoromethyldiphenylamine
2,6-dichloro-3,5-dimethyl-2',4'-dinitro-6'-trifluoromethyldiphenylamine
2-bromo-6-chloro-3,5-dimethyl-2',4'-dinitro-6'-trifluoromethyldiphenylamine
2,4,6-trifluoro-3,5-dimethyl-2',4'-dinitro-6'-trifluoromethyldiphenylamine
2,4-dichloro-6-fluoro-3,5-dimethyl-2',4'-dinitro-6'-trifluoromethyldiphenylamine
2,4-dibromo-3,5-dimethyl-2',4'-dinitro-6'-trifluoromethyldiphenylamine
2-chloro-4-fluoro-3,5-dimethyl-2',4'-dinitro-6'-trifluoromethyldiphenylamine
2-chloro-6-fluoro-3,5-dimethyl-2',4'-dinitro-6'-trifluoromethyldiphenylamine
2,6-dibromo-4-chloro-3,5-dimethyl-2',4'-dinitro-6'-trifluoromethyldiphenylamine
2,6-dibromo-4-fluoro-3,5-dimethyl-2',4'-dinitro-6'-trifluoromethyldiphenylamine
2,4-difluoro-3,5-dimethyl-2',4'-dinitro-6'-trifluoromethyldiphenylamine
2,6-dibromo-3,5-dimethyl-2',4'-dinitro-6'-trifluoromethyldiphenylamine
4-bromo-2,6-dichloro-3,5-dimethyl-2',4'-dinitro-6'-trifluoromethyldiphenylamine
2,6-difluoro-3,5-dimethyl-2',4'-dinitro-6'-trifluoromethyldiphenylamine
4-bromo-2,6-difluoro-3,5-dimethyl-2',4'-dinitro-6'-trifluoromethyldiphenylamine
2-bromo-6-fluoro-3,5-dimethyl-2',4'-dinitro-6'-trifluoromethyldiphenylamine
2,6-dibromo-2',4'-dinitro-3,5,6'-tris(trifluoromethyl)diphenylamine
2,4,6-trichloro-2',4'-dinitro-3,5,6'-tris(trifluoromethyl)diphenylamine
2,4-dibromo-2',4'-dinitro-3,5,6'-tris(trifluoromethyl)diphenylamine
2-bromo-6-chloro-2',4'-dinitro-3,5,6'-tris(trifluoromethyl)diphenylamine
2,6-dibromo-4-chloro-2',4'-dinitro-3,5,6'-tris(trifluoromethyl)diphenylamine
2,4-dichloro-2',4'-dinitro-3,5,6'-tris(trifluoromethyl)diphenylamine
2,6-dibromo-2',4'-dinitro-3,5,6'-tris(trifluoromethyl)diphenylamine
2,4,6-tribromo-2',4'-dinitro-3,5,6'-tris(trifluoromethyl)diphenylamine
2,4-dichloro-2',4'-dinitro-3,5,6'-tris(trifluoromethyl)diphenylamine
2,6-dichloro-2',4'-dinitro-3,5,6'-tris(trifluoromethyl)diphenylamine
2-bromo-4-chloro-2',4'-dinitro-3,5,6'-tris(trifluoromethyl)diphenylamine
2-chloro-6-bromo-2',4'-dinitro-3,5,6'-tris(trifluoromethyl)diphenylamine
2-chloro-4,6-dibromo-2',4'-dinitro-3,5,6'-tris(trifluoromethyl)diphenylamine
4-bromo-2-chloro-2',4'-dinitro-3,5,6'-tris(trifluoromethyl)diphenylamine
4-bromo-2,6-dichloro-2',4'-dinitro-3,5,6'-tris(trifluoromethyl)diphenylamine
2,4-dinitro-2',3',6-tris(trifluoromethyl)diphenylamine
4-chloro-2',4'-dinitro-2,3,6'-tris(trifluoromethyl)diphenylamine
4,6-dichloro-2',4'-dinitro-2,3,6'-tris(trifluoromethyl)diphenylamine
2,3,4-tribromo-2',4'-dinitro-5,6,6'-tris(trifluoromethyl)diphenylamine
2-bromo-4-chloro-2',4'-dinitro-5,6,6'-tris(trifluoromethyl)diphenylamine
2-chloro-3-bromo-2',4'-dinitro-5,6,6'-tris(trifluoromethyl)diphenylamine
3-bromo-4-chloro-2',4'-dinitro-5,6,6'-tris(trifluoromethyl)diphenylamine
2,4-dinitro-2',4',6-tris(trifluoromethyl)diphenylamine
2,3,5-trichloro-2',4'-dinitro-4,6,6'-tris(trifluoromethyl)diphenylamine
2,5-dichloro-2',4'-dinitro-4,6,6'-tris(trifluoromethyl)diphenylamine
3,6-dichloro-2',4'-dinitro-2,4,6'-tris(trifluoromethyl)diphenylamine
2,3-dibromo-2',4'-dinitro-4,6,6'-tris(trifluoromethyl)diphenylamine
2-bromo-5-chloro-2',4'-dinitro-4,6,6'-tris(trifluoromethyl)diphenylamine
2-bromo-3-chloro-2',4'-dinitro-4,6,6'-tris(trifluoromethyl)diphenylamine
5-chloro-2-bromo-2',4'-dinitro-3,4,6'-tris(trifluoromethyl)diphenylamine
2,4-dinitro-2',5',6-tris(trifluoromethyl)diphenylamine
2,4,5-tribromo-2',4'-dinitro-3,6,6'-tris(trifluromethyl)diphenylamine
2-bromo-4,5-dichloro-2',4'-dinitro-3,6,6'-tris(trifluoromethyl)diphenylamine
2,4-dichloro-5-bromo-2',4'-dinitro-3,6,6'-tris(trifluoromethyl)diphenylamine
4-chloro-2',4'-dinitro-2,5,6'-tris(trifluoromethyl)diphenylamine
2,5-dibromo-2',4'-dinitro-3,6,6'-tris(trifluoromethyl)diphenylamine
4-bromo-2-chloro-2',4'-dinitro-3,6,6'-tris(trifluoromethyl)diphenylamine
4-bromo-3-chloro-2',4'-dinitro-2,5,6'-tris(trifluoromethyl)diphenylamine
2,4-dichloro-2',4'-dinitro-3,6,6'-tris(trifluoromethyl)diphenylamine
2-bromo-4-chloro-2',4'-dinitro-3,6,6'-tris(trifluoromethyl)diphenylamine
4-bromo-2',4'-dinitro-2,5,6'-tris(trifluoromethyl)diphenylamine
3-bromo-4-chloro-2',4'-dinitro-2,5,6'-tris(trifluoromethyl)diphenylamine
2,4-dinitro-2',6,6'-tris(trifluoromethyl)diphenylamine
4-bromo-2',4'-dinitro-2,6,6'-tris(trifluoromethyl)diphenylamine
3-chloro-2',4'-dinitro-2,6,6'-tris(trifluoromethyl)diphenylamine
3-chloro-2',4'-dinitro-2,6,6'-tris(trifluoromethyl)diphenylamine
3,5-dichloro-2',4'-dinitro-2,6,6'-tris(trifluoromethyl)diphenylamine
3,4-dibromo-2',4'-dinitro-2,6,6'-tris(trifluoromethyl)diphenylamine
4-chloro-3-bromo-2',4'-dinitro-2,6,6'-tris(trifluoromethyl)diphenylamine
3-bromo-4-chloro-2',4'-dinitro-2,6,6'-tris(trifluoromethyl)diphenylamine 3-bromo-5-chloro-2',4'-dinitro-2,6,6'-tris(trifluoromethyl)diphenylamine
3,4,5-trichloro-2',4'-dinitro-2,6,6'-tris(trifluoromethyl)diphenylamine
2,4-dinitro-3',5',6-tris(trifluoromethyl)diphenylamine
4-chloro-2',4'-dinitro-3,5,6-tris(trifluoromethyl)diphenylamine
2-chloro-2',4'-dinitro-3,5,6'tris(trifluoromethyl)diphenylamine
2-bromo-2',4'-dinitro-3,5,6'-tris(trifluoromethyl)diphenylamine
2,4-dinitro-3',4',6-tris(trifluoromethyl)diphenylamine
2-chloro-2',4'-dinitro-3,4,6'-tris(trifluoromethyl)diphenylamine
3-bromo-2',4'-dinitro-4,5,6'-tris(trifluoromethyl)diphenylamine
2-chloro-2',4'-dinitro-4,5,6'-tris(trifluoromethyl)diphenylamine
2,3,6-tribromo-2',4'-dinitro-4,5,6'-tris(trifluoromethyl)diphenylamine
5-bromo-2-chloro-2',4'-dinitro-3,4,6'-tris(trifluoromethyl)diphenylamine
2,6-dichloro-2',4'-dinitro-3,4,6'-tris(trifluoromethyl)diphenylamine
2-chloro-5-bromo-2',4'-dinitro-3,4,6'-tris(trifluoromethyl)diphenylamine
2-bromo-5,6-dichloro-2',4'-dinitro-3,4,6'-tris(trifluoromethyl)diphenylamine
2,3-dichloro-2',4'-dinitro-4,5,6'-tris(trifluoromethyl)diphenylamine
2,3-dichloro-2',4'-dinitro-4,5,6'-tris(trifluoromethyl)diphenylamine
5-bromo-2-chloro-2',4'-dinitro-3,4,6'-tris(trifluoromethyl)diphenylamine
2,4,4'-trinitro-2',5',6-tris(trifluoromethyl)diphenylamine
2-chloro-2',4,4'-trinitro-3,5,6'-tris(trifluoromethyldiphenylamine
2,4,4'-trinitro-2',6,6'-tris(trifluoromethyl)diphenylamine
4-cyano-2',4'-dinitro-2,5,6'-tris(trifluoromethyl)diphenylamine
3-bromo-2',4,4'-trinitro-2,5,6'-tris(trifluoromethyl)diphenylamine
2,6-dichloro-2',4,4'-trinitro-3,5,6'-tris(trifluoromethyl)diphenylamine
2-chloro-4-cyano-2',4'-dinitro-3,5,6'-tris(trifluoromethyl)diphenylamine
3-bromo-4-cyano-2',4'-dinitro-2,5,6'-tris(trifluoromethyl)diphenylamine
3-bromo-5-chloro-2',4,4'-trinitro-2,6,6'-tris(trifluoromethyl)diphenylamine
2,6-dibromo-2',4,4'-trinitro-3,6'-bis(trifluoromethyl)diphenylamine
4-cyano-2',4'-dinitro-2,6,6'-tris(trifluoromethyl)diphenylamine
2,6-dibromo-2',4,4'-trinitro-3,5,6'-tris(trifluoromethyl)diphenylamine
2,6-dichloro-2',4,4'-trinitro-3,6'-bis(trifluoromethyl)diphenylamine
4-cyano-2,6-dichloro-2',4'-dinitro-3,5,6'-tris(trifluoromethyl)diphenylamine
2-bromo-6-chloro-2',4,4'-trinitro-3,6'-bis(trifluoromethyl)diphenylamine
3-bromo-5-chloro-4-cyano-2',4'-dinitro-2,6,6'-tris(trifluoromethyl)diphenylamine
2,6-dibromo-4-cyano-2',4'-dinitro-3,5,6'-tris(trifluoromethyl)diphenylamine
2,6-dichloro-4-cyano-2',4'-dinitro-3,6'-bis(trifluoromethyl)diphenylamine
2,6-dibromo-4-cyano-2',4'-dinitro-3,6'-bis(trifluoromethyl)diphenylamine
2-bromo-4-cyano-2',4'-dinitro-3,6'-bis(trifluoromethyl)diphenylamine
2-chloro-4-cyano-2',4'-dinitro-3,6'-bis(trifluoromethyl)diphenylamine
2-bromo-4,6-dichloro-2',4'-dinitro-5,6'-bis(trifluoromethyl)diphenylamine
2,6-dibromo-2',4,4'-trinitro-5,6'-bis(trifluoromethyl)diphenylamine
2,3,6-trichloro-5-methyl-2',4,4'-trinitro-6'-trifluoromethyldiphenylamine
3-bromo-4-cyano-2,6-difluoro-5-methyl-2',4'-dinitro-6'-trifluoromethyldiphenylamine
2,6-dibromo-3-methyl-2',4,4'-trinitro-6'-trifluoromethyldiphenylamine
2,3,6-trichloro-4-cyano-5-methyl-2',4'-dinitro-6'-trifluoromethyldiphenylamine
3-bromo-2,6-difluoro-5-methyl-2',4,4'-trinitro-6'-trifluoromethyldiphenylamine
2,6-dibromo-4-cyano-3,5-dimethyl-2',4'-dinitro-6'-trifluoromethyldiphenylamine
2-bromo-6-chloro-3-methyl-2',4,4'-trinitro-6'-trifluoromethyldiphenylamine
2,6-dibromo-4-cyano-3-methyl-2',4'-dinitro-6'-trifluoromethyldiphenylamine
2-bromo-6-chloro-4-cyano-3-methyl-2',4'-dinitro-6'-trifluoromethyldiphenylamine
2,4-dichloro-3,6-dibromo-2',4',6'-trinitrodiphenylamine
2-chloro-5-fluoro-2'-trifluoromethyl-4,4',6'-trinitrodiphenylamine
2,6-dinitro-2',3',4',5',6'-pentachloro-4-trifluoromethyldiphenylamine
2,3,5,6-tetrachloro-2'-trifluoromethyl-4,4',6'-trinitrodiphenylamine
2,5-dichloro-3-fluoro-2',4',6'-trinitrodiphenylamine
4-bromo-2,3,5,6-tetrachloro-2',4',6'-trinitordiphenylamine
2,4-dinitro-2',3',4',5',6'-pentabromo-6-trifluoromethyldiphenylamine
2,4'-bis(trifluoromethyl)-4,6-dinitro-2',3',5',6'-tetrachlorodiphenylamine
2-bromo-4,6-dichloro-N-propyl-2',4',6'-trinitrodiphenylamine
3,6-dibromo-2-chloro-2',4-bis(trifluoromethyl)-4',6'-dinitrodiphenylamine
2,3,5,6-tetrafluoro-2',4',6'-trinitrodiphenylamine
2,5-dichloro-3,6-difluoro-2'-trifluoromethyl-4,4',6'-trinitrodiphenylamine
3,5-difluoro-2',4'-dinitro-6'-trifluoromethyldiphenylamine
3,5-difluoro-2',4,4'-trinitro-6'-trifluoromethyldiphenylamine
2,4-dichloro-3,5-difluoro-6-methyl-2',4'-dinitro-6'-trifluoromethyldiphenylamine
2,4,6-trichloro-3,5-difluoro-2',4'-dinitro-6'-trifluoromethyldiphenylamine
2,4-dibromo-3,5-difluoro-2',4'-dinitro-6'-trifluoromethyldiphenylamine
4-chloro-2,2',4'-trinitro-6'-trifluoromethyldiphenylamine
2,2',4,4'-tetranitro-6'-trifluoromethyldiphenylamine
2,4-dibromo-2',4',6-trinitro-6'-trifluoromethyldiphenylamine 2,4-dichloro-3-methyl-2',4',6-trinitro-6'-trifluoromethyldiphenylamine
2,3,5-tribromo-2',4,4',6-tetranitro-6'-trifluoromethyldiphenylamine
2,4-dibromo-2',4',6-trinitro-3,6'-bis(trifluoromethyl)-diphenylamine The preferred compounds for use in the present invention are the following.
2,4,6-tribromo-2',4',6'-trinitrodiphenylamine
2,4,6-trichloro-N-methyl-2',4',6'-trinitrodiphenylamine
2,4,6-tribromo-N-methyl-2',4',6'-trinitrodiphenylamine
2,3,4,5,6-pentachloro-2',4'-dinitro-6'-trifluoromethyldiphenylamine
2,4-dichloro-2',4',6,6'-tetranitrodiphenylamine
3,5-bis(trifluoromethyl)-2',4',6'-trinitrodiphenylamine
2,3,4,5,6-pentachloro-2',4',6'-trinitrodiphenylamine
2,3,4,5,6-pentafluoro-2',4',6'-trinitrodiphenylamine
2,4-dibromo-6-chloro-2',4'-dinitro-6'-trifluoromethyldiphenylamine
2,4-dinitro-3',5',6-tris(trifluoromethyl)diphenylamine
4-bromo-2,6-dichloro-2',4'-dinitro-6'-trifluoromethyldiphenylamine
2,4-dinitro-4',6-bis(trifluoromethyl)diphenylamine
2-bromo-4,6-dichloro-2',4'-dinitro-6'-trifluoromethyldiphenylamine
2,4-dinitro-2',4',6'-trichloro-6-trifluoromethyldiphenylamine
2,4,6-trichloro-2',4',6'-trinitrodiphenylamine
2,4,6-tribromo-2',4'-dinitro-6'-trifluoromethyldiphenylamine The compounds used in the practice of this invention are easily synthesized by the reaction of a phenyl halide bearing trinitro or dinitro-trifluoromethyl substituents with an appropriately-substituted aniline. The reaction is a simple amination and is readily accomplished according to the known methods. An acid scavenger, such as an inorganic base, a tertiary amine or excess of the aniline intermediate, is needed in the reaction mixture. In general, the most convenient reaction medium is dimethylformamide at about −10° C., and sodium hydride is the best acid scavenger.

The starting substituted anilines and phenyl halides are readily obtained by methods which are commonly known in the chemical literature. For the convenience of the chemist, the following references discussing the synthesis of substituted anilines are mentioned. Finger et al., J. Am. Chem. Soc. 81, 94–101 (1959); McBee et al., J. Am. Chem. Soc. 73, 3932–34 (1951); Finger et al., J. Am. Chem. Soc. 73, 145–49 (1951); Bachman et al., J. Am. Chem. Soc. 69, 2022–25 (1957); Dains, J. Am. Chem. Soc. 52, 1573 (1930).

The trifluoromethyl-substituted anilines are best prepared, as chemists will recognize, by first obtaining a carboxylic acid-substituted aniline having the acid groups at the locations of the desired trifluoromethyls. The acid group is fluorinated with sulfur tetrafluoride according to the process of Hasek et al., Chemistry of Sulfur Tetrafluoride, J. Am. Chem. Soc. 82, 543–551 (1960).

It will be understood that the fluorinated aniline compounds are often prepared by first making a diazonium fluoroborate salt at the position where the fluorine atom is desired. The salt is then decomposed with heat to leave a fluorine atom at the desired position. Alternatively, it has recently been found that fluorine atoms may be inserted in phenyl rings with elemental fluorine at very low temperatures.

In some instances, it is convenient to use a starting aniline which lacks some or all of the halogen substituents of the desired product. The diphenylamine is formed by coupling the aniline with the appropriate phenyl halide, and the desired halogen substitutents are added by the common methods, as with the elemental halogen in acetic acid or methylene chloride.

Iodination is best carried out with iodine monochloride as the reagent. Such iodinations are discussed, for example, by Ginsberg, J. Am. Chem. Soc. 75, 1107 (1953), and by Johnson et al., Org. Syn., Coll. Vol. 2, 343 (1943).

When a compound having no 4-substitutent is to be made, it will often be necesssary to block the 4-position before halogenating. It is most convenient to use a sulfonic acid group as the blocking group, because it is readily added and readily removed. See, for example, Sandler and Karo, Organic Functional Group Preparations, 506–24 (Academic Press 1968); and Wagner and Zook, Synthetic Organic Chemistry, 15 (Wiley 1953).

The above two-step process is often particularly convenient for making the N-alkyl compounds. In such cases, one of the starting compounds is an N-alkylaniline, which is coupled with a trinitrophenyl halide to form the desired N-alkyldiphenylamine lacking some or all of the halogen substituents of the desired product. Halogenation produces the desire N-alkyldiphenylamine. Alternatively, in other instances it is convenient to form the N-H diphenylamine, and then to alkylate with an agent such as a dialkylsulfate or an alkyl halide.

Further description of the synthetic process may be found in South African Patent 73/09415.

The typical preparations below are shown to assure that organic chemists can obtain any of the compounds used in this invention.

EXAMPLE I 2,4,6-trichloro-2',4',6'-trinitrodiphenylamine

A 3 g. portion of sodium hydride was suspended in 50 ml. of dry dimethylformamide, and the suspension was cooled to −10° C. The temperature was held constant during the following steps. A solution of 10 g. of 2,4,6-trichloroaniline in 75 ml. of dry dimethylformamide was added to the suspension over a 15-minute period. The reaction mixture was then stirred for 45 minutes, after which a solution of 12.6 g. of picryl chloride in 75 ml. of dimethylformamide was added over a period of 20 minutes. The mixture was then allowed to stir and warm to 16° C. over a period of 90 minutes. The mixture was then poured over ice, and the resulting aqueous suspension was acidified with dilute hydrochloric acid. The solids were separated from the mixture by filtration, and were recrystallized from ethanol. The product, 10.8 g. of 2,4,6-trichloro-2',4',6'-trinitrodiphenylamine, m.p. 176°–177° C., was identified by nuclear magnetic resonance analysis, infrared analysis, and elemental microanalysis, with the following results.

|   | Theoretical | Found |
|---|---|---|
| C | 35.37% | 35.16% |
| H | 1.24 | 1.36 |
| N | 13.75 | 13.72 |
| O | 23.55 | 21.52 |
| Cl | 26.10 | 26.34 |

Similar synthetic methods are used to prepare the other compounds useful in this invention. For example, the following typical compounds were prepared according to the processes taught above. For each compound, the melting point and the approximate percentage yields are given.

EXAMPLE 2

2,6-dinitro-3',4,5'-tris(trifluoromethyl)diphenylamine, m.p. 150° C., yield 35%

EXAMPLE 3

3,5-bis(trifluoromethyl)-2',4',6'-trinitrodiphenylamine, m.p. 180°–181° C., yield 82%

EXAMPLE 4

2,3,4,5,6-pentachloro-2',4',6'-trinitrodiphenylamine, m.p. 234° C., yield 95%

EXAMPLE 5

2,6-dinitro-2',3',4',5',6'-pentachloro-4-trifluoromethyldiphenylamine, m.p. 203°–205° C., yield 56%

EXAMPLE 6

2,4,5-trichloro-2',4',6'-trinitrodiphenylamine, m.p. 198°–200° C., yield 40%

EXAMPLE 7

3,4,5-trichloro-2',4',6'-trinitrodiphenylamine, m.p. 201°–203° C., yield 61%

EXAMPLE 8

2,3,4,5,6-pentafluoro-2',4',6'-trinitrodiphenylamine, m.p. 117°–119° C., yield 24%

EXAMPLE 9

2,4-dinitro-2',4',6'-trichloro-6-trifluoromethyldiphenylamine, m.p. 106°–108° C., yield 26%

EXAMPLE 10

2,6-dichloro-2',4,4',6'-tetranitrodiphenylamine, m.p. 157°–159° C., yield 63%

EXAMPLE 11

2,4,6-tribromo-2',4'-dinitro-6'-trifluoromethyldiphenylamine, m.p. 153°–155° C., yield 60%

EXAMPLE 12

2,3,5,6-tetrachloro-2',4',6'-trinitrodiphenylamine, m.p. 192.5°–193.5° C., yield 58%

EXAMPLE 13

2,4,6-tribromo-2',4',6'-trinitrodiphenylamine, m.p. 220°–221° C., yield 52%

EXAMPLE 14

2,3,5,6-tetrafluoro-2',4',6'-trinitrodiphenylamine, m.p. 113°–115° C., yield 25%

EXAMPLE 15

2,3,4,5,6-pentachloro-2',4'-dinitro-6'-trifluoromethyldiphenylamine, m.p. 172°–172.5° C., yield 65%

EXAMPLE 16

2,4-dichloro-2',4',6,6'-tetranitrodiphenylamine, m.p. 187°–189° C., yield 37%

EXAMPLE 17

2,4-dinitro-4',6-bis(trifluoromethyl)diphenylamine, m.p. 113° C., yield 16%

EXAMPLE 18

2,5-dichloro-2',4'-dinitro-6'-trifluoromethyldiphenylamine, m.p. 133°–134° C., yield 45%

EXAMPLE 19

2,6-dichloro-2',4'-dinitro-6'-trifluoromethyldiphenylamine, m.p. 93°–95° C., yield 35%

EXAMPLE 20

2,4,6-trifluoro-2',4'-dinitro-6'-trifluoromethyldiphenylamine, m.p. 104°–105° C., yield 15%

EXAMPLE 21

2,4-dichloro-2',4'-dinitro-6'-trifluoromethyldiphenylamine, m.p. 99.5°–101° C., yield 10%

EXAMPLE 22

2,3,5,6-tetrachloro-2',4'-dinitro-6'-trifluoromethyldiphenylamine, m.p. 172°–173° C., yield 70%

EXAMPLE 23

2,6-dibromo-2',4'-dinitro-4,6'-bis(trifluoromethyl)diphenylamine, m.p. 125.5°–127° C., yield 8%

EXAMPLE 24

4-chloro-2',4'-dinitro-6'-trifluoromethyldiphenylamine, m.p. 104°–105° C., yield 50%

EXAMPLE 25

2,6-dibromo-2',4'-dinitro-6'-trifluoromethyldiphenylamine, m.p. 127°–128° C., yield 30%

EXAMPLE 26

3,4-dichloro-2',4'-dinitro-6'-trifluoromethyldiphenylamine, m.p. 111°–112° C., yield 3%

EXAMPLE 27

4-cyano-2',4'-dinitro-6'-trifluoromethyldiphenylamine, m.p. 199°–200° C., yield 8%

EXAMPLE 28

4-bromo-2',4'-dinitro-6'-trifluoromethyldiphenylamine, m.p. 118°–119° C., yield 20%

EXAMPLE 29

4-iodo-2',4'-dinitro-6'-trifluoromethyldiphenylamine, m.p. 138°–139.5° C., yield 10%

EXAMPLE 30

2,4-dibromo-2',4'-dinitro-6'-trifluoromethyldiphenylamine, m.p. 124.5°–126° C., yield 17%

EXAMPLE 31

2,4-difluoro-2',4'-dinitro-6'-trifluoromethyldiphenylamine, m.p. 89.5°–90° C., yield 25%

EXAMPLE 32

2,5-difluoro-2',4'-dinitro-6'-trifluoromethyldiphenylamine, m.p. 100°–101° C., yield 32%

EXAMPLE 33

3,5-dichloro-2',4'-dinitro-6'-trifluoromethyldiphenylamine, m.p. 136°–138° C., yield 10%

EXAMPLE 34

2,4-dinitro-3',5',6-tris(trifluoromethyl)diphenylamine, m.p. 136°–137° C., yield 15%

EXAMPLE 35

2,3,4,5,6-pentafluoro-2',6'-dinitro-4'-trifluoromethyldiphenylamine, m.p. 120°–120.5° C., yield 75%

The following example typifies the preparation of compounds by a two-step procedure, where the diphenylamine is first formed and one of the phenyl rings is then halogenated.

EXAMPLE 36

2,4,6-trichloro-N-methyl-2',4',6'-trinitrodiphenylamine

Three g. of sodium hydride as a 50% dispersion in oil was dispersed in 50 ml. of dry dimethylformamide, and the suspension was cooled to −10° under nitrogen. The temperature was maintained approximately constant throughout the process. A solution of 10 g. of N-methylaniline in 50 ml. of dimethylformamide was then added over a period of 16 minutes. After the mixture was stirred for 1½ hours, a solution of 23.1 g. of picryl chloride in 75 ml. of dimethylformamide was added over a 25-minute period. The mixture was allowed to stir and warm to room temperature overnight.

The reaction mixture was then poured over a large amount of crushed ice, and the aqueous mixture was acidified with hydrochloric acid and was allowed to stand overnight. The mixture was then filtered, and the solids were recrystallized from denatured ethanol to produce 10.2 g. of N-methyl-2,4,6-trinitrodiphenylamine, m.p. 104°–105° C.

A 2.3 g. portion of the above interemediate was suspended in 30 ml. of acetic acid, and the mixture was saturated with gaseous chlorine with stirring at room temperature. After 3 hours of constant stirring with slow addition of chlorine, the reaction mixture was poured into water and the resulting yellow precipitate was filtered out of the mixture. The filtrate was stirred with magnesium sulfate and charcoal, filtered and evaporated to dryness. The residue was taken up in diethyl ether-petroleum ether, and the insoluble portions were removed by filtration. Recrystallization of the product by evaporation of the solvents produced 0.48 g. of 2,4,6-trichloro-N-methyl-2',4',6'-trinitrodiphenylamine, m.p. 178°–179.5° C.

|    | Theoretical | Found  |
|----|-------------|--------|
| C  | 37.04%      | 37.24% |
| H  | 1.67        | 1.87   |
| N  | 13.29       | 13.42  |
| Cl | 25.23       | 24.99  |

Similarly, the example below illustrates the use of two stages of halogenation.

EXAMPLE 37

2,4-dibromo-6-chloro-N-methyl-2',4',6'-trinitrodiphenylamine

A 1.3 g. portion of the diphenylamine intermediate of Example 36 was suspended in 10 ml. of acetic acid and stirred at room temperature for 2 hours with 1 ml. of elemental bromine. The mixture was then poured into water and filtered. The solids were taken up in 20 ml. of acetic acid, warmed slightly and saturated with chlorine. After 1½ hours of stirring with occasional addition of chlorine, a light yellow precipitate formed, which was separated by filtration. The solids were identified as 0.72 g. of 2,4-dibromo-6-chloro-N-methyl-2',4',6'-trinitrodiphenylamine, m.p. 199°–200° C.

|    | Theoretical | Found  |
|----|-------------|--------|
| C  | 30.59%      | 30.74% |
| H  | 1.38        | 1.51   |
| N  | 10.98       | 10.75  |
| Cl | 6.95        | 6.99   |

The following additional compounds are typical of those most readily prepared by the processes typified by Examples 36 and 37.

EXAMPLE 38

2,4,6-trichloro-N-ethyl-2',4',6'-trinitrodiphenylamine, m.p. 138°–140° C., yield 60%

|    | Theoretical | Found  |
|----|-------------|--------|
| C  | 38.60%      | 38.90% |
| H  | 2.08        | 2.03   |
| N  | 12.86       | 13.10  |
| O  | 24.42       | 24.71  |
| Cl | 22.04       | 21.94  |

EXAMPLE 39

2,4-dibromo-6-chloro-2',4'-dinitro-6'-trifluoromethyldiphenylamine, m.p. 129.5°–130.5° C., yield 50%

EXAMPLE 40

2,6-dichloro-4-iodo-2',4',6'-trinitrodiphenylamine, m.p. 202°–204° C., yield 12%

EXAMPLE 41

2,6-dichloro-4-cyano-2',4',6'-trinitrodiphenylamine, m.p. 216°–218° C., yield 4%

EXAMPLE 42

2,4-dichloro-6-methyl-2',4'-dinitro-6'-trifluoromethyldiphenylamine, m.p. 143°–144° C., yield 1%

EXAMPLE 43

2,4,6-trichloro-3,5-dimethyl-2',4'-dinitro-6'-trifluoromethyldiphenylamine, m.p. 156°–159° C., yield 42%

EXAMPLE 44

4-bromo-2,6-dichloro-2',4'-dinitro-6'-trifluoromethyldiphenylamine, m.p. 115°–115.5° C., yield 8%

The utility of this invention has been investigated by administering the compounds to rats in laboratory tests. The following reports of typical tests illustrate the outstanding rodenticidal efficacy of the compounds of this invention.

The tests were performed by mixing the compounds with an animal feed of cereal origin, and presenting the treated feeds to male albino rats of the Sprague-Dawley strain.

The tables below report the concentration of the compound in the feed, in parts per million parts of feed (ppm.), the number of days after starting the rats on treated feed when each rat died, and the weight change, positive or negative, of each rate during the 10-day experiment.

Juvenile rats weighing 50–60 g. were used in some tests, and older rats up to about 250 g. were used in others. The weight gains of the untreated control rats varied widely from experiment to experiment, because of the varying ages and sizes of the rats. In all instances, however, controls made weight gains in the vicinity of 40 to 60 g. per animal during the experimental period.

| Rat No. | Day of Death | Weight Change |
|---|---|---|
| 1 | 3 | −9 g. |
| 2 | 7 | −15 g. |
| 3 | 4 | −15 g. |
| 4 | 6 | −13 g. |
| 5 | 3 | −5 g. |

Compound of Example 2, 200 ppm.

| Rat No. | Day of Death | Weight Change |
|---|---|---|
| 1 | Survived | 14 g. |
| 2 | Survived | 21 g. |
| 3 | Survived | 19 g. |
| 4 | Survived | 58 g. |
| 5 | 10 | −7 g. |

Compound of Example 3, 200 ppm.

| Rat No. | Day of Death | Weight Change |
|---|---|---|
| 1 | 2 | −12 g. |
| 2 | 3 | −21 g. |
| 3 | 2 | −12 g. |
| 4 | 2 | −12 g. |
| 5 | 2 | −18 g. |

Compound of Example 4, 25 ppm.

| Rat No. | Day of Death | Weight Change |
|---|---|---|
| 1 | 2 | −7 g. |
| 2 | 5 | −12 g. |
| 3 | 4 | −12 g. |
| 4 | 2 | −4 g. |
| 5 | 4 | −7 g. |

Compound of Example 5, 200 ppm.

| Rat No. | Day of Death | Weight Change |
|---|---|---|
| 1 | 1 | −8 g. |
| 2 | 3 | −18 g. |
| 3 | 2 | −10 g. |
| 4 | 4 | −14 g. |
| 5 | 3 | −16 g. |

Compound of Example 6, 100 ppm.

| Rat No. | Day of Death | Weight Change |
|---|---|---|
| 1 | 7 | −18 g. |
| 2 | 10 | −16 g. |
| 3 | 9 | −23 g. |
| 4 | 10 | −17 g. |
| 5 | 8 | −17 g. |

Compound of Example 7, 200 ppm.

| Rat No. | Day of Death | Weight Change |
|---|---|---|
| 1 | 8 | −23 g. |
| 2 | 6 | −18 g. |
| 3 | 4 | −10 g. |

-continued

| Rat No. | Day of Death | Weight Change |
|---|---|---|
| 4 | Survived | −14 g. |

Compound of Example 8, 100 ppm.

| Rat No. | Day of Death | Weight Change |
|---|---|---|
| 1 | 2 | −10 g. |
| 2 | 1 | −3 g. |
| 3 | 2 | −6 g. |
| 4 | 3 | −7 g. |
| 5 | 2 | −9 g. |

Compound of Example 9, 200 ppm.

| Rat No. | Day of Death | Weight Change |
|---|---|---|
| 1 | 1 | −10 g. |
| 2 | 1 | −8 g. |
| 3 | 1 | −11 g. |
| 4 | 1 | −6 g. |
| 5 | 1 | −3 g. |

Compound of Example 10, 200 ppm.

| Rat No. | Day of Death | Weight Change |
|---|---|---|
| 1 | 2 | −11 g. |
| 2 | 1 | −7 g. |
| 3 | 2 | −7 g. |
| 4 | 2 | −12 g. |
| 5 | 2 | −10 g. |

Compound of Example 11, 25 ppm.

| Rat No. | Day of Death | Weight Change |
|---|---|---|
| 1 | 2 | −10 g. |
| 2 | 2 | −12 g. |
| 3 | 1 | −2 g. |
| 4 | 1 | −10 g. |
| 5 | 1 | −6 g. |

Compound of Example 13, 25 ppm.

| Rat No. | Day of Death | Weight Change |
|---|---|---|
| 1 | 6 | −20 g. |
| 2 | 4 | −21 g. |
| 3 | 4 | −20 g. |
| 4 | 3 | −13 g. |
| 5 | 2 | −3 g. |

Compound of Example 16, 50 ppm.

| Rat No. | Day of Death | Weight Change |
|---|---|---|
| 1 | 6 | −19 g. |
| 2 | 2 | −3 g. |
| 3 | 4 | −21 g. |
| 4 | 4 | −13 g. |
| 5 | 2 | −5 g. |

Compound of Example 20, 500 ppm.

| Rat No. | Day of Death | Weight Change |
|---|---|---|
| 1 | 6 | −68 g. |
| 2 | 7 | −90 g. |

-continued

| Rat No. | Day of Death | Weight Change |
|---|---|---|
| 3 | 9 | −100 g. |
| 4 | 5 | −66 g. |
| 5 | 7 | −72 g. |

Compound of Example 21, 500 ppm.

| Rat No. | Day of Death | Weight Change |
|---|---|---|
| 1 | 5 | −70 g. |
| 2 | 3 | −43 g. |
| 3 | 1 | −17 g. |
| 4 | 3 | −63 g. |
| 5 | 4 | −67 g. |

Compound of Example 36, 25 ppm.

| Rat No. | Day of Death | Weight Change |
|---|---|---|
| 1 | 2 | −8 g. |
| 2 | 4 | −19 g. |
| 3 | 6 | −18 g. |
| 4 | 4 | −24 g. |
| 5 | 6 | −20 g. |

Compound of Example 37, 30 ppm.

| Rat No. | Day of Death | Weight Change |
|---|---|---|
| 1 | 6 | −19 g. |
| 2 | 5 | −13 g. |
| 3 | 4 | −12 g. |
| 4 | 3 | −12 g. |
| 5 | 4 | −10 g. |

Compound of Example 38, 25 ppm.

| Rat No. | Day of Death | Weight Change |
|---|---|---|
| 1 | 7 | −86 g. |
| 2 | 7 | −60 g. |
| 3 | 5 | −46 g. |
| 4 | 5 | −46 g. |
| 5 | 5 | −35 g. |

The excellent rodenticidal results produced by the compounds are obvious on the face of the data. It will be observed that the compounds are effective at very low concentrations. Further, it is most significant that the compounds kills the rats with certainty, but not immediately. As has been explained, a good rodenticide allows time for many or all of the rats or mice of a colony to consume the poison bait before animals begin to die. It is clear that the compounds of this invention, when used in proper concentrations, work in the desired sure, but delayed, manner.

In its most broad description, this invention provides a method of reducing a population of rats or mice which comprises supplying to a locus frequented by the rats or mice a rodenticidally-effective amount of a rodenticidal composition which comprises an effective rodenticidal concentration of a compound described above. The invention also provides the rodenticidal compositions which comprise inert carriers and effective rodenticidal concentrations of the compounds described above.

The details of the method, such as the times and places in which the rodenticidal compositions are supplied, and the carriers of the rodenticidal compositions, are common to the rodenticidal art. Some explanation of the various ways in which the method is carried out will be presented, however, for the convenience of the reader.

The method is effective in the control of rats and mice in general. For example, such pestiferous species as the following are controlled by the proper use of the present invention.

House mouse (*Mus musculus*)
Norway rat (*Rattus norvegicus*)
Black rat (*R. rattus rattus*)
Roof rat (*R. r. frugivorus*)
White-footed mouse (*Peromyscus leucopus*)
Pack rat (*Neotoma cinearea*)
Meadow mouse (*Microtus pennsylvanicus*)

Those skilled in th rodenticidal art will understand that the present invention can also be used for the control of rodents other than rats and mice. Since rodents other than rats and mice are frequently beneficial, the control of such other rodents is not contemplated as a regular part of the benefit of this invention. However, should the control of other rodents be desirable in particular circumstances, the invention can be used therefor.

This invention effectively controls rats and mice by both acute and chronic toxicity techniques. Proper adjustment of the concentration of the compound in the rodenticidal composition, as those of skill in the art will understand, allows the invention to reduce a population of rats or mice either by immediately poisoning the animals, or by chronically poisioning them over a number of feedings.

As has been explained, however, the delayed lethal effect of the compounds taught herein is an important factor in their rodenticidal usefulness. The maximum benefit of this invention is obtained by supplying to the locus of the rats or mice a rodenticidal composition which contains a concentration of the compound which is not acutely lethal in a single feeding, but which contributes to a lethal effect in the course of at least two feedings, and preferably a larger number of feedings. Accordingly it is also preferred to supply a sufficiently large amount of the rodenticidal composition to allow all the members of the population to feed on the composition two or more times.

A rat consumes about 5 to 50 grams of food per day; a mouse consumes about 1 to 5 grams per day, depending in each case of the animal's age, size, and state of health. A pest control specialist can estimate the number of animals in a colony, and can supply to the locus of the animals appropriate quantities of treated feed, or other compositions, to provide an effective amount for each animal.

A preferred embodiment of the invention is, therefore, a method for reducing a population of rats or mice which comprises supplying to a locus frequented by the rats or mice a sufficient quantity for two or more feedings of a rodenticidal composition which comprises a sufficient concentration of a compound described above to be effectively rodenticidal upon two or more feedings. Another preferred embodiment of the invention is the rodenticidal composition just described.

Although the invention is described herein in terms of "feedings", the invention is also used by supplying rodenticidal compositions in the forms of tracking powders and drinking water compositions. It will be understood that such compositions are used in the same way as compositions based on foodstuffs, making appropriate adjustments to accommodate for the difference in the way the rodents ingest the compositions. The concentrations of the compounds in preferred drinking water or tracking powder compositions are effectively rodenticidal upon two or more waterings or cleanings, respectively. The term "feeding" is used herein to include watering and cleaning.

Rodenticidal compositions are based on inert carriers which include foodstuffs, drinking water and finely powdered solids. Compositions based on foodstuffs, which are the preferred inert carriers, may comprise any edible substance, since rats and mice are omnivorous. For example, such compositions may comprise cereals, meat byproducts or fats. Cereal foodstuffs which can be used in rodenticidal compositions include such substances as oatmeal, ground or cracked corn, soybean products, wheat and wheat byproducts, waste rice, and the like. Any grain can be the basis of such compositions. Sweetening and flavor-enhancing agents can also be added to increase the attraction of the bait.

Fatty rodenticidal bait compositions are regularly made in inert ingredients such as peanut butter, other nut butters, milk solids, animal fats, vegetable oils and the like. Rodenticidal compositions are also sometimes based on animal products such as bone meal and on meat products including animal byproducts.

Tracking powders are composed of rodenticidal compounds dispersed in powdered solids. Virtually any powder can be used, including talc, chalk, ground clays, flour, nut shell flour, and the like including powdered stone.

Rodenticidal compositions in drinking water comprise suspensions or dispersions of the compounds. The compounds are quite water-insoluble, and it is therefore normally necessary to grind the compound to a fine particle size and suspend it. Suspending agents are commonly used in the pharmaceutical art, and are chosen from among the thickeners, such as carboxymethylcellulose, polyvinylpyrrolidone, gelatin and the alginates, and the surfactants, such as lecithin, alkylphenol polyethylene oxide adducts, alkyl sulfates, naphthalenesulfonates, alkylbenzenesulfonates and the polyoxyethylene sorbitan esters. It is sometimes also possible to use silicone antifoams, glycols, sorbitol and sugars as suspending agents.

The time when a rodenticidal composition of this invention is supplied to the locus of a colony of rats or mice is not critical. There are no seasons when a rodent colony is particularly susceptible, or relatively immune, to the use of rodenticides. It is usually advantageous first to pre-bait the colony with an untreated composition. Preferably, sufficient of the treated composition should be supplied to last for the time during which the members of the colony feed at least twice.

The concentration of the compound in the composition depends on the identity of the compound chosen, since they are of different potencies, upon the rapidity with which the population is desired to be reduced, and upon other factors as well. For example, if the population can be isolated, so that its only food or water source is a rodenticidal composition, the concentration obviously should be lower than if a variety of food sources are available. In general, rodenticidal compositions should contain concentrations from 5 to about 2000 parts per million parts of the composition (ppm.). More preferably, concentrations from about 10 to about 500 ppm. should be used, although it will be understood that amounts both above and below the named range will be effective and even desirable in unusual circumstances.

It will be understood that additives and attractants can be usefully included in rodenticidal compositions of this invention. Such additives as, for example, odorants, sex hormones, and flavoring agents are regularly used in rodenticidal compositions, and can usefully be used in the compositions of this invention to assist in breaking down the suspicion of the rodents.

I claim:

1. A method of reducing a population of rats or mice which comprises supplying to a locus frequented by the rate or mice a rodenticidally-effective amount of a rodenticidal composition comprising an inert carrier and a rodenticidally-effective concentration of a compound of the formula

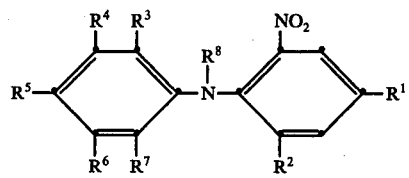

wherein one of $R^1$ and $R^2$ represents nitro and the other represents trifluoromethyl or nitro;

$R^8$ represents hydrogen, methyl, ethyl or propyl, provided that $R^8$ represents hydrogen when either $R^1$ or $R^2$ represents trifluoromethyl;

(1) when $R^1$ represents trifluoromethyl,
$R^3$, $R^4$, $R^5$, $R^6$ and $R^7$ all represent chloro, all represent bromo, or all represent fluoro, or $R^4$ and $R^6$ represent trifluoromethyl and $R^3$, $R^5$ and $R^7$ represent hydrogen;

(2) when $R^2$ represents trifluoromethyl,
$R^5$ represents halo, hydrogen, cyano, nitro, methyl or trifluoromethyl;
$R^3$ and $R^7$ independently represent chloro, bromo, fluoro, methyl, trifluoromethyl, nitro or hydrogen;
$R^4$ and $R^6$ independently represent chloro, bromo, fluoro, methyl, trifluoromethyl or hydrogen; provided that
  (a) when $R^3$, $R^4$, $R^6$ and $R^7$ all represent hydrogen, $R^5$ does not represent fluoro, methyl or hydrogen;
  (b) when $R^5$ represents hydrogen, no more than two of $R^3$, $R^4$, $R^6$ and $R^7$ represent hydrogen;
  (c) no more than two of $R^3$, $R^4$, $R^5$, $R^6$ and $R^7$ represent trifluoromethyl;
  (d) when one and only one of $R^3$, $R^4$, $R^6$ and $R^7$ represents trifluoromethyl, two or three of $R^3$, $R^5$ and $R^7$ represent chloro or bromo;
  (e) no more than one of $R^3$, $R^4$, $R^5$, $R^6$ and $R^7$ represents methyl, except that $R^4$ and $R^6$ both may represent methyl;
  (f) when $R^3$, $R^4$, $R^5$, $R^6$ or $R^7$ represents methyl, two or three of $R^3$, $R^5$ and $R^7$ represent chloro, bromo or fluoro;
  (g) no more than one of $R^3$ and $R^7$ represents nitro;
  (h) when $R^3$ or $R^7$ represents nitro, $R^5$ represents chloro, bromo or nitro;

(3) when both $R^1$ and $R^2$ represent nitro and $R^8$ represents hydrogen,
$R^5$ represents halo, hydrogen, cyano, nitro or trifluoromethyl;
$R^3$ and $R^7$ independently represent bromo, chloro, fluoro, hydrogen or nitro;

$R^4$ and $R^6$ independently represent chloro, bromo, fluoro, trifluoromethyl or hydrogen; provided that
(a) no more than two of $R^3$, $R^4$, $R^5$, $R^6$ and $R^7$ represent hydrogen, except that $R^3$, $R^5$ and $R^7$ all represent hydrogen when $R^4$ and $R^6$ both represent trifluoromethyl;
(b) no more than one of $R^3$, $R^5$ and $R^7$ represents nitro;
(c) when two of $R^3$, $R^4$, $R^5$, $R^6$ and $R^7$ represent hydrogen, they are not adjacent to each other;
(d) when either $R^3$ or $R^7$ represents nitro, neither $R^5$ nor the other of $R^3$ and $R^7$ represents hydrogen;
(e) $R^5$ does not represent cyano, nitro or trifluoromethyl when $R^4$ or $R^6$ represents trifluoromethyl;
(4) when $R^8$ does not represent hydrogen, $R^3$, $R^4$, $R^5$, $R^6$ and $R^7$ independently represent chloro, bromo, fluoro or hydrogen, provided that no more than two of $R^3$, $R^4$, $R^5$, $R^6$ and $R^7$ represent hydrogen, and two such hydrogen atoms are not adjacent to each other; provided that, in classes 3) and 4) above,
(a) when one of $R^3$, $R^4$, $R^5$, $R^6$ and $R^7$ represents fluoro, two or three of $R^3$, $R^5$ and $R^7$ represent chloro or bromo; and provided that, in classes 2), and 3) and 4) above,
(a) when one of $R^3$, $R^4$, $R^5$, $R^6$ and $R^7$ represents trifluoromethyl, none of $R^3$, $R^4$, $R^5$, $R^6$ and $R^7$ represents fluoro or methyl.

2. A method of claim 1 wherein the concentration of the compound is from about 5 to about 2000 ppm.

3. A method of claim 2 wherein the concentration of the compound is from about 10 to about 500 ppm.

4. A method of claim 1 wherein the concentration of the compound is rodenticidally effective upon two or more feedings, and the amount of the composition is sufficient for two or more feedings.

5. A method of claim 4 wherein $R^1$ and $R^2$ represent nitro and $R^8$ represents hydrogen.

6. A method of claim 5 wherein $R^5$ represents chloro, bromo, fluoro, hydrogen or trifluoromethyl.

7. A method of claim 6 wherein $R^3$ and $R^7$ independently represent bromo, chloro, fluoro or nitro.

8. A method of claim 7 wherein $R^4$ and $R^6$ independently represent chloro, bromo, fluoro or hydrogen.

9. The method of claim 8 wherein the compound is 2,4,6-tribromo-2',4',6'-trinitrodiphenylamine.

10. The method of claim 8 wherein the compound is 2,4-dichloro-2',4',6,6'-tetranitrodiphenylamine.

11. The method of claim 8 wherein the compound is 2,3,4,5,6-pentachloro-2',4',6'-trinitrodiphenylamine.

12. The method of claim 8 wherein the compound is 2,3,4,5,6-pentafluoro-2',4',6'-trinitrodiphenylamine.

13. The method of claim 8 wherein the compound is 2,4,6-trichloro-2',4',6'-trinitrodiphenylamine.

14. A method of claim 6 wherein $R^3$ and $R^7$ independently represent bromo, chloro, fluoro or hydrogen and $R^4$ and $R^6$ independently represent chloro, bromo, fluoro or trifluoromethyl.

15. The method of claim 14 wherein the compound is 3,5-bis(trifluoromethyl)-2',4',6'-trinitrodiphenylamine.

16. A method of claim 4 wherein $R^1$ and $R^2$ both represent nitro and $R^8$ represents methyl, ethyl or propyl.

17. A method of claim 16 wherein $R^8$ represents methyl.

18. A method of claim 17 wherein $R^3$, $R^5$ and $R^7$ independently represent chloro, bromo, or fluoro.

19. A method of claim 18 wherein $R^4$ and $R^6$ independently represent chloro, bromo, or hydrogen.

20. A method of claim 19 wherein $R^3$, $R^5$ and $R^7$ independently represent chloro or bromo.

21. The method of claim 20 wherein the compound is 2,4,6-trichloro-N-methyl-2',4',6'-trinitrodiphenylamine.

22. The method of claim 20 wherein the compound is 2,4,6-tribromo-N-methyl-2',4',6'-trinitrodiphenylamine.

23. A method of claim 20 wherein $R^4$ and $R^6$ independently represent chloro or bromo.

24. A method of claim 4 wherein $R^2$ represents trifluoromethyl and $R^8$ represents hydrogen.

25. A method of claim 24 wherein $R^5$ represents halo, hydrogen, cyano, nitro or trifluoromethyl.

26. A method of claim 25 wherein $R^3$, $R^4$, $R^6$ and $R^7$ independently represent chloro, bromo, fluoro, trifluoromethyl or hydrogen.

27. A method of claim 26 wherein $R^5$ represents halo, hydrogen or trifluoromethyl.

28. The method of claim 27 wherein the compound is 2,4-dinitro-3',5',6-tris(trifluoromethyl)diphenylamine.

29. The method of claim 27 wherein the compound is 2,4-dinitro-4',6-bis(trifluoromethyl)diphenylamine.

30. A method of claim 27 wherein $R^3$, $R^4$, $R^6$ and $R^7$ independently represent chloro, bromo, fluoro or hydrogen.

31. A method of claim 30 wherein $R^5$ represents chloro or bromo.

32. A method of claim 31 wherein the compound is 2,3,4,5,6-pentachloro-2',4'-dinitro-6'-trifluoromethyldiphenylamine.

33. The method of claim 31 wherein the compound is 2,4-dinitro-2',4',6'-trichloro-6-trifluoromethyldiphenylamine.

34. The method of claim 31 wherein the compound is 2,4,6-tribromo-2',4'-dinitro-6'-trifluoromethyldiphenylamine.

35. The method of claim 31 wherein the compound is 2,4-dibromo-6-chloro-2',4'-dinitro-6'-trifluoromethyldiphenylamine.

36. The method of claim 31 wherein the compound is 4-bromo-2,6-dichloro-2',4'-dinitro-6'-trifluoromethyldiphenylamine.

37. The method of claim 31 wherein the compound is 2-bromo-4,6-dichloro-2',4'-dinitro-6'-trifluoromethyldiphenylamine.

* * * * *

UNITED STATES PATENT AND TRADEMARK OFFICE
CERTIFICATE OF CORRECTION

PATENT NO. : 4,084,004

DATED : April 11, 1978

INVENTOR(S) : Barry Allen Dreikorn

It is certified that error appears in the above-identified patent and that said Letters Patent are hereby corrected as shown below:

Column 1, line 13, the first occurrence of "or" should read

--of--.

Column 2, line 30, "or" should read --of--.

Column 16, line 59, "-bistrifluoromethyl)-" should read

-- -bis(trifluoromethyl)- --.

Column 22, line 41, "2',4',6'-trinitordi-" should read

--2',4',6'-trinitrodi- --.

Column 24, line 29, "desire" should read --desired--.

Column 28, line 65, "rate" should read --rat--.

Column 29, after line 5, add --Compound of Example 1, 15 ppm--.

Column 31, line 48, "kills" should read --kill--.

UNITED STATES PATENT AND TRADEMARK OFFICE
CERTIFICATE OF CORRECTION

PATENT NO. : 4,084,004
DATED : April 11, 1978
INVENTOR(S) : Barry Allen Dreikorn It is certified that error appears in the above-identified patent and that said Letters Patent are hereby corrected as shown below:

Column 32, line 13, "cinearea" should read --cinerea--.

Column 32, line 15, "th" should read --the--.

Column 32, line 30, "poisioning" should read --poisoning--.

Column 34, line 13, Claim 1, "rate" should read --rats--.

Signed and Sealed this

Twenty-second Day of May 1979

[SEAL]

Attest:

RUTH C. MASON
Attesting Officer

DONALD W. BANNER
Commissioner of Patents and Trademarks